(12) United States Patent
Ji et al.

(10) Patent No.: US 9,700,207 B2
(45) Date of Patent: *Jul. 11, 2017

(54) METHODS, SYSTEMS, AND PRODUCTS FOR MEASURING HEALTH

(71) Applicant: AT&T Intellectual Property I, L.P., Atlanta, GA (US)

(72) Inventors: Lusheng Ji, Randolph, NJ (US); Robert R. Miller, II, Convent Station, NJ (US); Harry R. Worstell, Florham Park, NJ (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 41 days.

This patent is subject to a terminal disclaimer.

(21) Appl. No.: 14/179,625

(22) Filed: Feb. 13, 2014

(65) Prior Publication Data

US 2014/0163898 A1    Jun. 12, 2014

Related U.S. Application Data

(63) Continuation of application No. 12/844,262, filed on Jul. 27, 2010, now Pat. No. 8,666,768.

(51) Int. Cl.
*A61B 5/00* (2006.01)
*G06F 19/00* (2011.01)

(52) U.S. Cl.
CPC .......... *A61B 5/0015* (2013.01); *G06F 19/322* (2013.01)

(58) Field of Classification Search
CPC .... G06F 19/322; G06F 19/3406; G06Q 50/24
USPC ................................. 705/2, 3; 600/300, 301
See application file for complete search history.

(56) References Cited

U.S. PATENT DOCUMENTS

| | | |
|---|---|---|
| 4,838,275 A | 6/1989 | Lee |
| 4,933,873 A | 6/1990 | Kaufman et al. |
| 5,335,313 A | 8/1994 | Douglas |
| 5,442,728 A | 8/1995 | Kaufman et al. |
| 5,577,164 A | 11/1996 | Kaneko et al. |
| 5,923,763 A * | 7/1999 | Walker ................ G07D 7/0033 380/51 |
| 5,960,085 A | 9/1999 | De la Huerga |
| 6,014,626 A | 1/2000 | Cohen |
| 6,256,019 B1 | 7/2001 | Allport |
| 6,314,398 B1 | 11/2001 | Junqua |
| 6,411,933 B1 | 6/2002 | Maes et al. |
| 6,535,131 B1 | 3/2003 | Bar-Shalom et al. |
| 6,646,541 B1 | 11/2003 | Wang et al. |
| 6,885,736 B2 | 4/2005 | Uppaluru |
| 6,906,696 B2 | 6/2005 | Allport |
| 6,911,916 B1 | 6/2005 | Wang et al. |
| 6,968,223 B2 | 11/2005 | Hanover |
| 7,130,452 B2 | 10/2006 | Bolle et al. |

(Continued)

*Primary Examiner* — Elaine Gort
*Assistant Examiner* — John Go
(74) *Attorney, Agent, or Firm* — Scott P. Zimmerman, PLLC

(57) ABSTRACT

Methods, systems, and products measure health data related to a user. A time-stamped device identifier is received that uniquely identifies a communications device. A time-stamped sensor measurement is separately received. A difference in time between the time-stamped device identifier and the time-stamped sensor measurement is determined. When the difference in time is within a window of time, then the sensor measurement is associated with the device identifier.

20 Claims, 28 Drawing Sheets

(56) References Cited

U.S. PATENT DOCUMENTS

| | | |
|---|---|---|
| 7,143,044 B2 | 11/2006 | Zadrozny et al. |
| 7,155,371 B2 | 12/2006 | Kawatahara et al. |
| 7,228,213 B2 | 6/2007 | Sakai et al. |
| 7,292,139 B2 | 11/2007 | Mazar et al. |
| 7,310,668 B2 | 12/2007 | Brown |
| 7,315,821 B2 | 1/2008 | Monchi et al. |
| 7,338,443 B1* | 3/2008 | Tucker ............... G06F 19/3406 128/920 |
| 7,363,226 B2 | 4/2008 | Shiomi et al. |
| 7,399,276 B1 | 7/2008 | Brown et al. |
| 7,541,547 B2 | 6/2009 | McGuire et al. |
| 7,555,425 B2 | 6/2009 | Oon |
| 7,657,444 B2 | 2/2010 | Yu |
| 7,727,161 B2 | 6/2010 | Coyle et al. |
| 7,778,852 B2 | 8/2010 | Vasko et al. |
| 7,925,508 B1 | 4/2011 | Michaelis |
| 8,106,752 B2 | 1/2012 | Golden |
| 8,130,095 B2 | 3/2012 | Allen et al. |
| 8,140,340 B2 | 3/2012 | Bhogal et al. |
| 8,442,835 B2 | 5/2013 | Ji et al. |
| 2003/0069753 A1 | 4/2003 | Brown |
| 2003/0163299 A1 | 8/2003 | Iliff |
| 2004/0102683 A1* | 5/2004 | Khanuja ............... A61B 5/0002 600/300 |
| 2004/0162726 A1 | 8/2004 | Chang |
| 2004/0186747 A1 | 9/2004 | Nakano et al. |
| 2004/0204635 A1 | 10/2004 | Scharf et al. |
| 2004/0227050 A1 | 11/2004 | Haller |
| 2005/0010416 A1 | 1/2005 | Anderson et al. |
| 2005/0101841 A9 | 5/2005 | Kaylor et al. |
| 2005/0247494 A1 | 11/2005 | Montagnino |
| 2006/0015016 A1 | 1/2006 | Thornton |
| 2006/0149558 A1 | 7/2006 | Kahn et al. |
| 2006/0173684 A1 | 8/2006 | Fischer et al. |
| 2006/0173713 A1 | 8/2006 | Petro et al. |
| 2006/0215495 A1 | 9/2006 | Soled et al. |
| 2006/0293891 A1 | 12/2006 | Pathuel |
| 2007/0032345 A1 | 2/2007 | Padmanabhan et al. |
| 2007/0054252 A1 | 3/2007 | Lin |
| 2007/0061361 A1 | 3/2007 | Tanaka |
| 2007/0198264 A1 | 8/2007 | Chang |
| 2007/0247449 A1 | 10/2007 | Mack et al. |
| 2007/0276277 A1 | 11/2007 | Booth et al. |
| 2007/0294416 A1 | 12/2007 | Agre et al. |
| 2007/0299670 A1 | 12/2007 | Chang |
| 2008/0058651 A1* | 3/2008 | Shen .................... A61B 5/0031 600/481 |
| 2008/0082338 A1 | 4/2008 | O'Neil et al. |
| 2008/0097788 A1* | 4/2008 | Dang ................ G06F 19/328 705/2 |
| 2008/0097909 A1* | 4/2008 | Dicks .................... G06Q 50/24 705/50 |
| 2008/0103531 A1* | 5/2008 | Ginggen ........... A61M 5/14276 607/2 |
| 2008/0104649 A1 | 5/2008 | Naaman |
| 2008/0147439 A1 | 6/2008 | Maliszewski |
| 2008/0147604 A1 | 6/2008 | Bulow |
| 2008/0162185 A1 | 7/2008 | Klabunde et al. |
| 2008/0228057 A1 | 9/2008 | Graskov et al. |
| 2008/0255428 A1 | 10/2008 | Sharda et al. |
| 2008/0269571 A1 | 10/2008 | Brown et al. |
| 2009/0012816 A1 | 1/2009 | Cookson et al. |
| 2009/0097641 A1 | 4/2009 | Matsuzaki et al. |
| 2009/0118596 A1* | 5/2009 | Khanuja ............... A61B 5/0002 600/301 |
| 2009/0125401 A1 | 5/2009 | Beenau et al. |
| 2009/0144021 A1 | 6/2009 | Ketskes |
| 2009/0178858 A1 | 7/2009 | Daniels et al. |
| 2009/0204411 A1 | 8/2009 | Morikawa et al. |
| 2009/0210357 A1 | 8/2009 | Pudar et al. |
| 2009/0248822 A1 | 10/2009 | De Vriendt et al. |
| 2009/0270743 A1 | 10/2009 | Dugan et al. |
| 2009/0282371 A1 | 11/2009 | Curl |
| 2009/0306983 A1 | 12/2009 | Bhandari |
| 2010/0026817 A1 | 2/2010 | Ryan et al. |
| 2010/0033303 A1 | 2/2010 | Dugan et al. |
| 2010/0036662 A1 | 2/2010 | Emmons |
| 2010/0056876 A1 | 3/2010 | Ellis et al. |
| 2010/0070867 A1 | 3/2010 | Lemmers |
| 2010/0191075 A1 | 7/2010 | Angelides |
| 2010/0223285 A1 | 9/2010 | Biddulph-Krentar |
| 2010/0277274 A1 | 11/2010 | Toleti |
| 2010/0286490 A1 | 11/2010 | Koverzin |
| 2010/0293601 A1 | 11/2010 | Schultz |
| 2011/0035234 A1 | 2/2011 | Roe et al. |
| 2011/0082705 A1 | 4/2011 | Kobylevsky |
| 2011/0092779 A1 | 4/2011 | Chang et al. |
| 2011/0098544 A1 | 4/2011 | Shah et al. |
| 2011/0105919 A1 | 5/2011 | Naji |
| 2011/0119053 A1 | 5/2011 | Kuo et al. |
| 2011/0161076 A1 | 6/2011 | Davis et al. |
| 2011/0172994 A1 | 7/2011 | Lindahl et al. |
| 2011/0184735 A1 | 7/2011 | Flaks et al. |
| 2011/0190701 A1 | 8/2011 | Remde et al. |
| 2011/0260832 A1 | 10/2011 | Ross et al. |
| 2011/0273280 A1 | 11/2011 | Chang et al. |
| 2011/0276326 A1 | 11/2011 | Fumarolo et al. |
| 2011/0282671 A1 | 11/2011 | Dicks et al. |
| 2011/0301957 A1 | 12/2011 | Brown et al. |
| 2011/0313774 A1 | 12/2011 | Ji et al. |
| 2012/0030229 A1 | 2/2012 | Ji et al. |
| 2012/0109676 A1 | 5/2012 | Landau |
| 2012/0150545 A1 | 6/2012 | Simon |
| 2012/0218123 A1 | 8/2012 | Ji et al. |
| 2012/0219271 A1 | 8/2012 | Vunic et al. |
| 2012/0220276 A1 | 8/2012 | Kobylarz |
| 2012/0265535 A1 | 10/2012 | Bryant-Rich et al. |
| 2013/0138786 A1 | 5/2013 | Ji et al. |

\* cited by examiner

METHODS, SYSTEMS, AND PRODUCTS FOR MEASURING HEALTH

CROSS-REFERENCE TO RELATED APPLICATION

This application is a continuation of U.S. application Ser. No. 12/844,262 filed Jul. 27, 2010 and since issued as U.S. Pat. No. 8,666,768, and incorporated herein by reference in its entirety.

BACKGROUND

Exemplary embodiments generally relate to surgery, data processing, electrical communications, and weighing scales and, more particularly, to speech signal processing, speech control, health care management, measurement systems, voice recognition, and speaker identification and verification.

Remote monitoring of health is important. Blood pressure, glucose, weight, and other health factors may be measured from home using a medical measurement device. These health factors may then be communicated to a remote location (such as a doctor's office) for analysis and tracking. A common problem, though, is user binding. Many medical measurement devices are shared between multiple users. A household weight scale, for example, may be shared by multiple members of a household. The members of the household all use the same weight scale to measure their individual weights. If a weight measurement is not bound to the correct member of the household, the weight measurement may be erroneously associated with the wrong user.

BRIEF DESCRIPTION OF THE SEVERAL VIEWS OF THE DRAWINGS

The features, aspects, and advantages of the exemplary embodiments are better understood when the following Detailed Description is read with reference to the accompanying drawings, wherein.

DETAILED DESCRIPTION

The exemplary embodiments will now be described more fully hereinafter with reference to the accompanying drawings. The exemplary embodiments may, however, be embodied in many different forms and should not be construed as limited to the embodiments set forth herein. These embodiments are provided so that this disclosure will be thorough and complete and will fully convey the exemplary embodiments to those of ordinary skill in the art. Moreover, all statements herein reciting embodiments, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure).

Thus, for example, it will be appreciated by those of ordinary skill in the art that the diagrams, schematics, illustrations, and the like represent conceptual views or processes illustrating the exemplary embodiments. The functions of the various elements shown in the figures may be provided through the use of dedicated hardware as well as hardware capable of executing associated software. Those of ordinary skill in the art further understand that the exemplary hardware, software, processes, methods, and/or operating systems described herein are for illustrative purposes and, thus, are not intended to be limited to any particular named manufacturer.

As used herein, the singular forms "a," "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include wirelessly connected or coupled. As used herein, the term "and/or" includes any and all combinations of one or more of the associated listed items.

It will also be understood that, although the terms first, second, etc. may be used herein to describe various elements, these elements should not be limited by these terms. These terms are only used to distinguish one element from another. For example, a first device could be termed a second device, and, similarly, a second device could be termed a first device without departing from the teachings of the disclosure.

Figure 1:
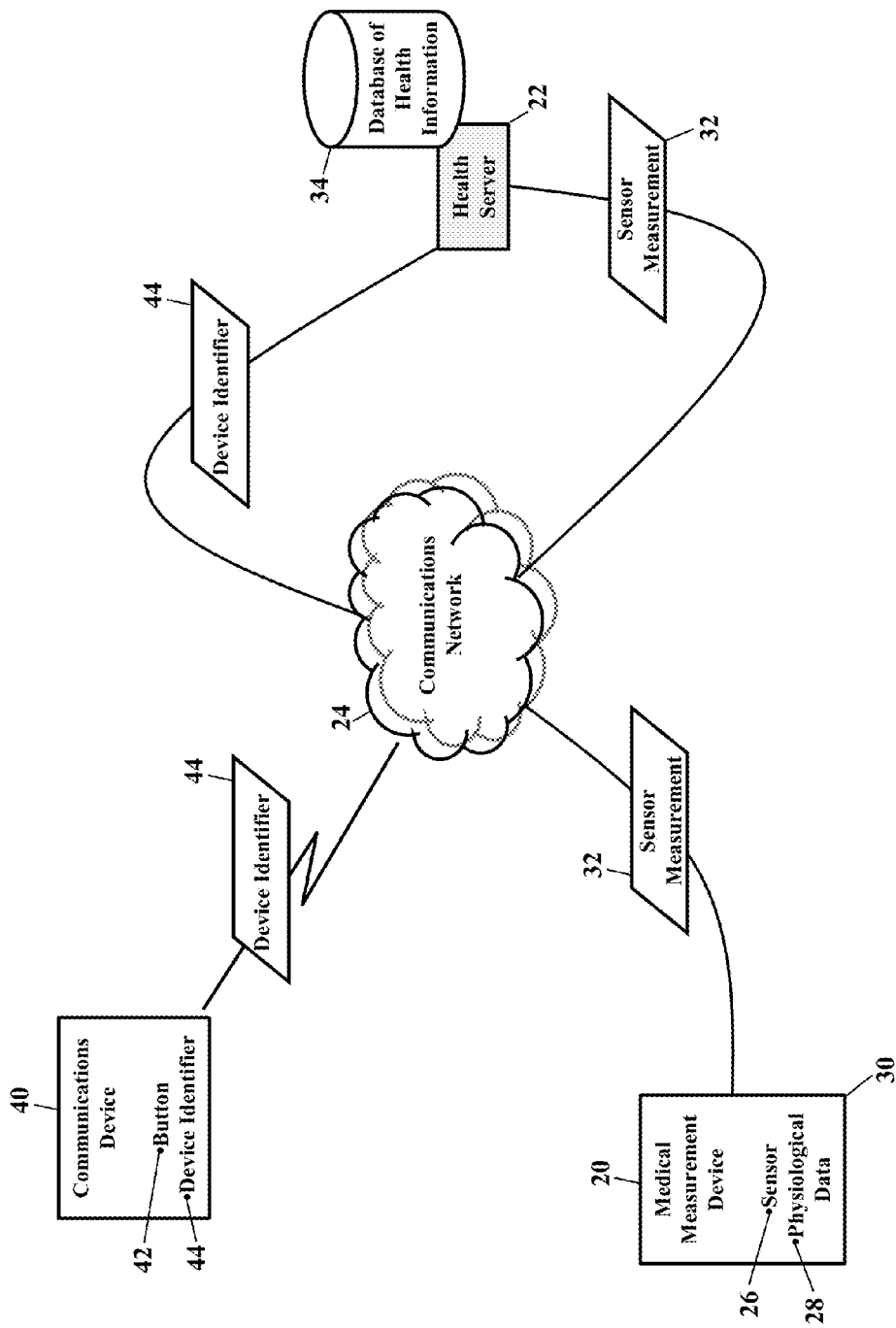
FIG. 1 is a simplified schematic illustrating an environment in which exemplary embodiments may be implemented.

FIG. 1 is a simplified schematic illustrating an environment in which exemplary embodiments may be implemented. FIG. 1 illustrates a client-server network architecture that remotely monitors a user's health factors. A medical measurement device 20 communicates with a health server 22 via a communications network 24. The medical measurement device 20 has a sensor 26 that measures any physiological data 28 related to a user's health condition.

The medical measurement device 20 and/or the sensor 26 may measure, for example, the user's weight, blood pressure, temperature, pulse rate, glucose level, height, cholesterol level, respiratory rate, or any other information or data related to the user's physiological condition. For simplicity, though, the medical measurement device 20 will be described as a bathroom weight scale 30. The sensor 26 may thus measure the user's weight. The user steps on a footpad to obtain a weight reading. When the sensor 26 measures the user's weight, the medical measurement device 20 sends a sensor measurement 32 to the health server 22. The health server 22 stores the sensor measurement 32 in a database 34 of health information.

The sensor measurement 32, though, should be bound to the user. Even though the sensor measurement 32 has been received at the health server 22, the sensor measurement 32 must be associated to the correct user. Because the medical measurement device 20 is often shared among many people, the sensor measurement 32 must be correctly identified with the corresponding user. The bathroom weight scale 30, for example, is usually shared by multiple members of a household. The household members all use the same weight scale to measure their individual weights. If a weight measurement is confused with the wrong user, the health server 22 may incorrectly associate the sensor measurement 32 with the wrong user.

Exemplary embodiments, then, bind the sensor measurement 32 to the correct user. As FIG. 1 illustrates, a separate communications device 40 also communicates with the health server 22 via the communications network 24. As the medical measurement device 20 obtains the sensor measurement 32, the user also makes some input to the communications device 40. The input, for example may be pushing a button 42 on the communications device 40. The communications device 40 wirelessly or physically communicates with the communications network 24 and is capable of receiving some input or indication from the user. The communications device 40 sends a device identifier 44 to an address in the communications network 24 that is associated with the health server 22. The device identifier 44 uniquely identifies the communications device 40 associated with the user. When the health server 22 receives the device identifier 44, the health server 22 may bind or associate the sensor measurement 32 to the device identifier 44 of the user's communications device 40. The health server 22 may thus store the sensor measurement 32 in the database 34 of health information, and the sensor measurement 32 is associated or mapped to the device identifier 44 of the user's communications device 40.

The binding is further explained using the bathroom weight scale 30. As the above paragraphs explained, the medical measurement device 20 may be the bathroom weight scale 30 that measure's the user's weight. When the user steps on the bathroom weight scale 30, the user also makes an input to the user's communications device 40. The communications device 40 may be a phone, laptop computer, remote control, key fob, or any other processor-controlled device (as later paragraphs will explain). The communications device 40 sends the device identifier 44 to the health server 22, and the bathroom weight scale 30 separately sends the sensor measurement 32 to the health server 22. The health server 22 associates the sensor measurement 32 to the device identifier 44 of the user's communications device 40. Exemplary embodiments thus permit the health server 22 to accurately associate the sensor measurement 32 to the communications device 40 that sent the device identifier 44. Because the device identifier 44 uniquely identifies the communications device 40, the health server 22 may even identify a human user of the communications device 40. The health server 22 thus accurately associates each user's weight measurement in the database 34 of health information.

Exemplary embodiments may be applied regardless of networking environment. The communications network 24 may be a cable network operating in the radio-frequency domain and/or the Internet Protocol (IP) domain. The communications network 24, however, may also include a distributed computing network, such as the Internet (sometimes alternatively known as the "World Wide Web"), an intranet, a local-area network (LAN), and/or a wide-area network (WAN). The communications network 24 may include coaxial cables, copper wires, fiber optic lines, and/or hybrid-coaxial lines. The communications network 24 may even include wireless portions utilizing any portion of the electromagnetic spectrum and any signaling standard (such as the I.E.E.E. 802 family of standards, GSM/CDMA/TDMA or any cellular standard, and/or the ISM band). The communications network 24 may even include powerline portions, in which signals are communicated via electrical wiring. The concepts described herein may be applied to any wireless/wireline communications network, regardless of physical componentry, physical configuration, or communications standard(s).

Figure 2:
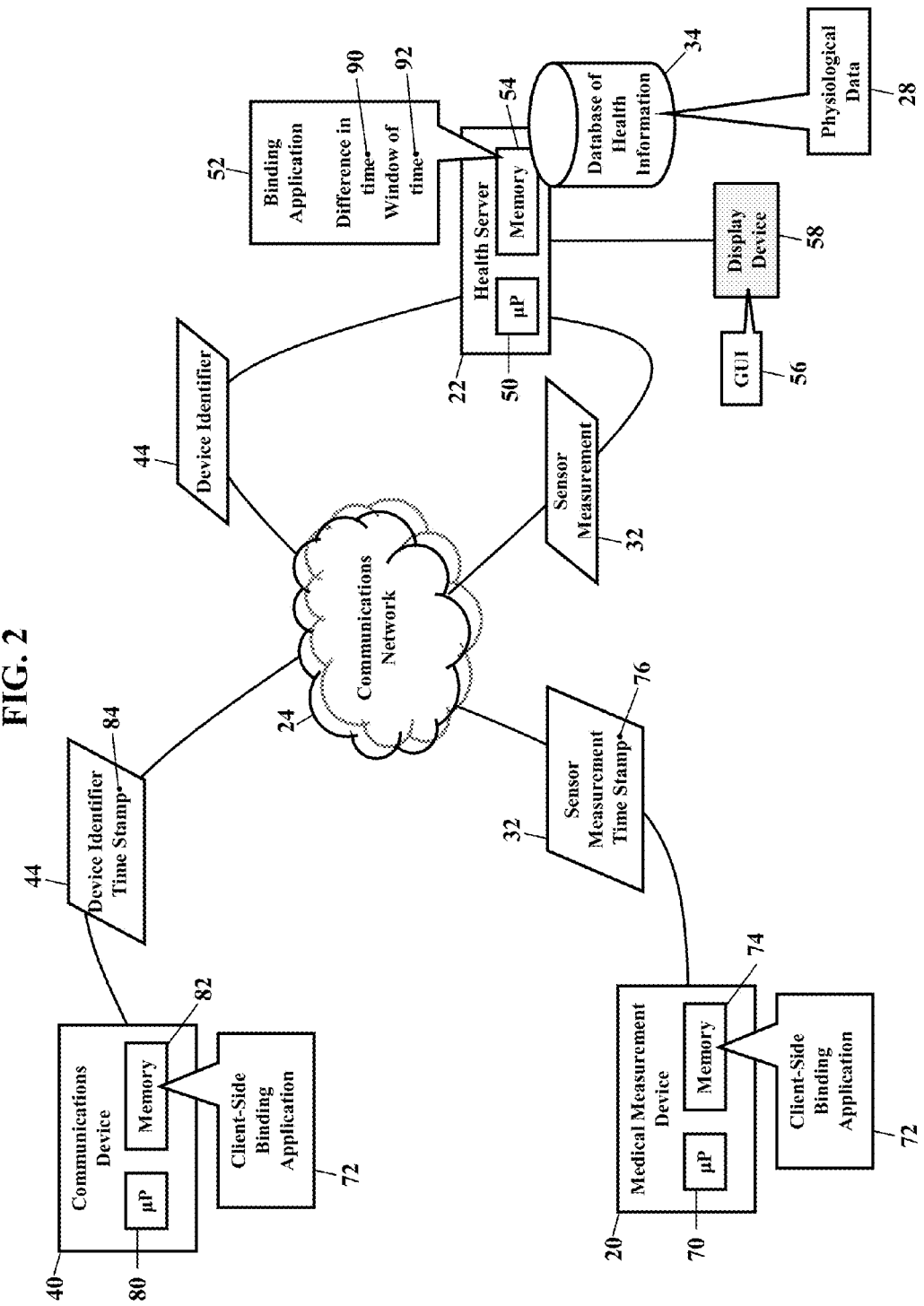
FIGS. 2 and 3 are more detailed schematics illustrating the operating environment, according to exemplary embodiments.
Figure 3:
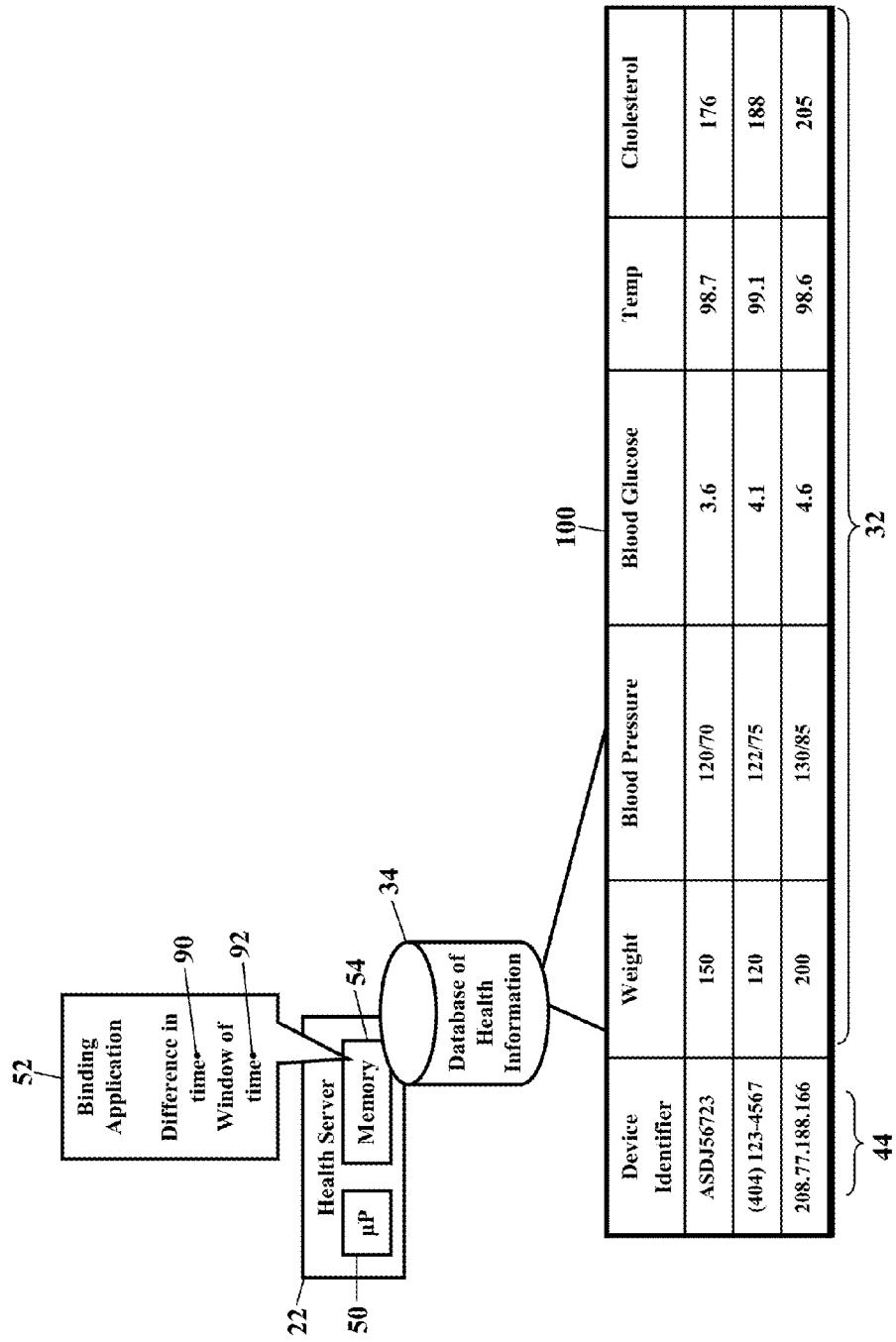

FIGS. 2 and 3 are more detailed schematics illustrating the operating environment, according to exemplary embodiments. Here the health server 22 has a processor 50 (e.g., "µP"), application specific integrated circuit (ASIC), or other component that executes a binding application 52 stored in a memory 54. The binding application 52 may cause the processor 50 to produce a graphical user interface ("GUI") 56. The graphical user interface 56 is illustrated as being visually produced on a display device 58, yet the graphical user interface 56 may also have audible features. The binding application 52, however, may operate in any processor-controlled device, as later paragraphs will explain.

The health server 22 receives the sensor measurement 32 from the medical measurement device 20. The medical measurement device 20 has a processor 70 (e.g., "µP"), application specific integrated circuit (ASIC), or other component that executes a client-side binding application 72 stored in a memory 74. The client-side binding application 72 may cooperate with the binding application 52 to send the sensor measurement 32 to the address associated with the health server 22. The sensor measurement 32 may include a time stamp 76. The time stamp 76 may be added by the client-side binding application 72 and may thus represent a date/time of generation by the medical measurement device 20. The time stamp 76, however, may be added by the binding application 52 upon receipt at the health server 22.

The health server 22 also receives the device identifier 44 from the user's communications device 40. The user's communications device 40 also has a processor 80 (e.g., "µP"), application specific integrated circuit (ASIC), or other component that also executes the client-side binding application 72 stored in a memory 82. The client-side binding application 72 may again cooperate with the binding application 52 to send the device identifier 44 to the address associated with the health server 22. The device identifier 44 may also include a time stamp 84. The time stamp 84 may be added by the client-side binding application 72, or the time stamp 84 may be added by the binding application 52 upon receipt at the health server 22.

The binding application 52 then correctly associates the sensor measurement 32 to the device identifier 44. The binding application 52 determines a difference 90 in time between the time-stamped device identifier 44 and the time-stamped sensor measurement 32. The binding application 52 compares the difference 90 in time to a window 92 of time. The window 92 of time may be a configurable or definable parameter for binding the sensor measurement 32 to the device identifier 44. The window 92 of time may be retrieved from the memory 54 of the health server. When the difference 90 in time is within the window 92 of time, then the sensor measurement 32 may be confidently bound to the device identifier 44 that uniquely identifies the user's communications device 40. The binding application 52 may thus associate the sensor measurement 32 to the user's communications device 40 and, thus, to the user.

The window 92 of time is confidence. If the time-stamped sensor measurement 32 and the time-stamped device identifier 44 are contemporaneous, then the binding application 52 is assured that the sensor measurement 32 relates to the user's communications device 40. If the time-stamped sensor measurement 32 is stale compared to the time-stamped device identifier 44, then the binding application 52 may not be assured that the sensor measurement 32 relates to the user. The greater the difference 90 in time (between the time-stamped device identifier 44 and the time-stamped sensor measurement 32), then less relation may exist between communications device 40 (and the user) and the sensor measurement 32. If the difference 90 in time lies within the window 92 of time, then the binding application 52 may associate the sensor measurement 32 to the device identifier 44 of the user's communications device 40. When, however, the difference 90 in time lies outside the window 92 of time, then the binding application 52 may consider the sensor measurement 32 to be indeterminable to any user. The binding application 52 may thus decline to associate the sensor measurement 32 to the device identifier 44.

FIG. 3 further illustrates the database 34 of health information. The health server 22 builds and/or accesses the database 34 of health information. The database 34 of health information is illustrated as being locally stored in the memory 54 of the health server 22, but the database 34 of health information may be remotely accessed and maintained at any location in communications network (illustrated as reference numeral 24 in FIG. 1). Regardless, the database 34 of health information stores the sensor measurements 32 associated with different device identifiers 44 of different communications devices. FIG. 3, for example, illustrates the database 34 of health information as a table 100 that maps, relates, or otherwise associates the sensor measurements 32 to different device identifiers 44. Each sensor measurement 32 represents some physiological data (illustrated as reference numeral 28 in FIGS. 1-2) associated with the device identifier 44. Each sensor measurement 32, for example, may indicate the user's weight, blood pressure, temperature, pulse rate, glucose level, height, cholesterol level, respiratory rate, or any other information or data related to the user's physiological condition. When the difference 90 in time (between the time-stamped device identifier 44 and the time-stamped sensor measurement 32) is less than or equal to the window 92 of time (in seconds or minutes, for example), then the binding application 52 associates the sensor measurement 32 to the device identifier 44 of the user's communications device 40. The health server 22 thus accurately associates each user's sensor measurement 32 in the database 34 of health information.

Figure 4:
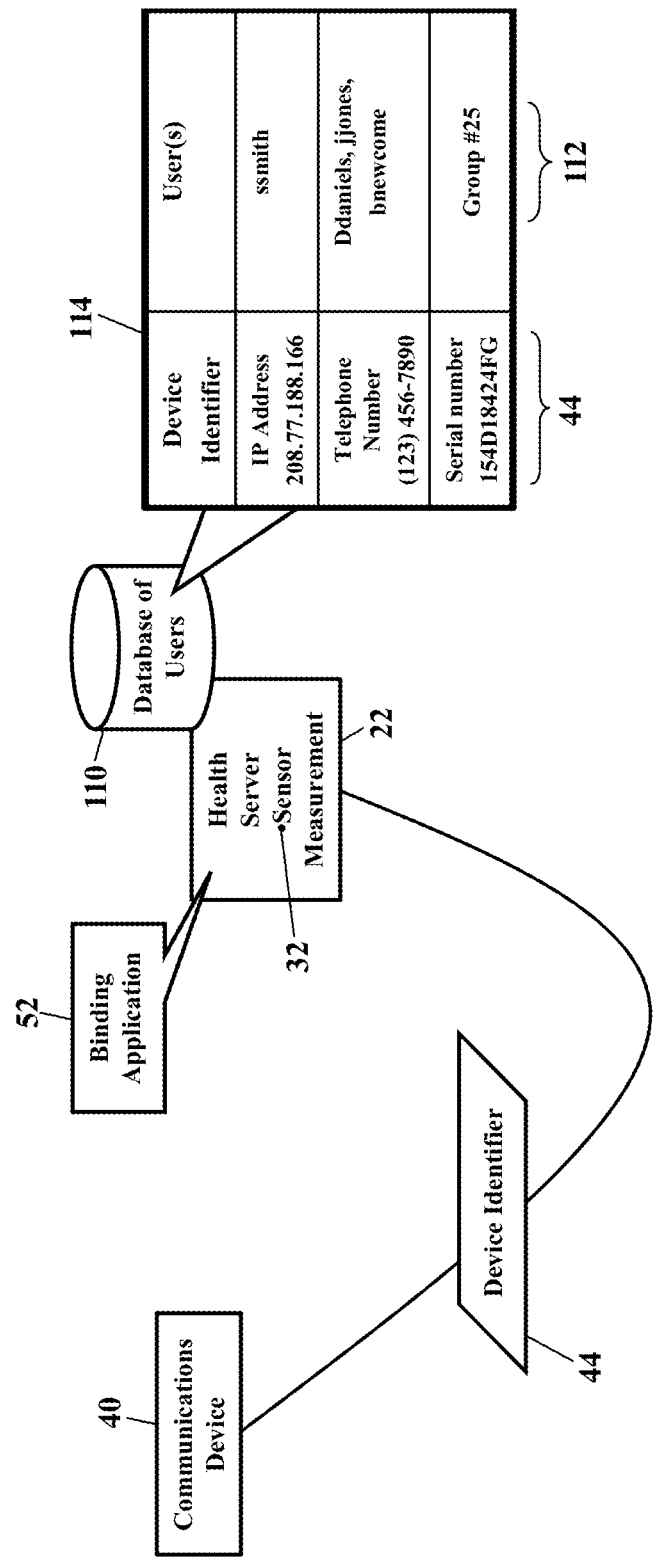
FIG. 4 is a schematic illustrating a device identifier, according to exemplary embodiments.
Figure 5:
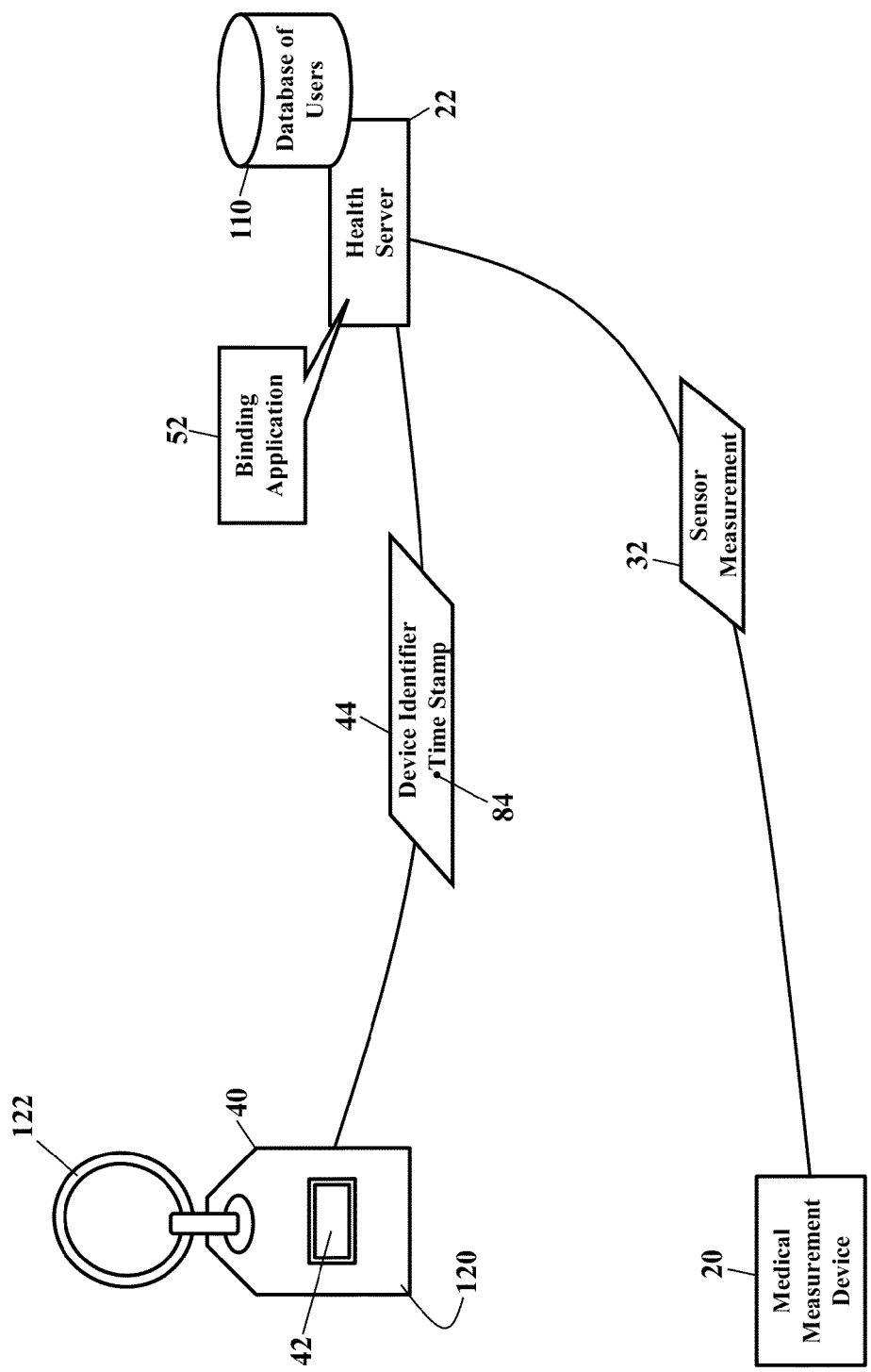
FIGS. 5-8 are schematics illustrating a key fob, according to exemplary embodiments.

FIG. 4 is a schematic further illustrating the device identifier 44, according to exemplary embodiments. The device identifier 44 uniquely identifies the communications device 40 that sent the device identifier 44. The device identifier 44 may be a serial number, Internet Protocol address, telephone number, or any other alphanumeric string or combination. When the health server 22 receives the device identifier 44, the binding application 52 may use the device identifier 44 to bind the sensor measurement 32 to the correct user.

The binding application 52 may then query a database 110 of users. The database 110 of users stores associations between device identifiers 44 and users 112. Once the device identifier 44 is known, the database 110 of users may reveal a single user, or even a group of users, that are associated with the communications device 40. Most cell phones, intelligent phones, personal digital assistants, and other communications devices are owned and used by a single user. However, some computers, gaming devices, televisions, and remote controls are shared by multiple users. If multiple users share the same communications device 40, then multiple users may be associated to the device identifier 44 of the shared communications device 40. The database 110 of users, for example, is illustrated as being locally stored in the health server 22, but the database 110 of users may be remotely accessed. The database 110 of users is illustrated as a table 114 that maps, relates, or otherwise associates the device identifier 44 to one or more users 112. The binding application 52 queries the database 110 of users for the device identifier 44 and retrieves the single user, or a group of users, that is/are associated with the device identifier 44 of the communications device 40.

FIGS. 5-8 are schematics illustrating a key fob 120, according to exemplary embodiments. Here the user's communications device 40 is illustrated as the key fob 120 that may be hung from the user's key ring 122. The user makes some input to the key fob 120 that is contemporaneous to the sensor measurement 32 at the medical measurement device 20 (as the above paragraphs explained). The key fob 120, for example, may have one or more of the buttons 42. As the medical measurement device 20 obtains the sensor measurement 32, the user also depresses the button 42 on the key fob 120. The key fob 120 wirelessly sends the device identifier 44 to the health server 22. The key fob 120 may also add the time stamp 84. The time stamp 84 may indicate the time that the button 42 was depressed, the time the device identifier 44 was sent/transmitted, or any other timing reference.

Figure 6:
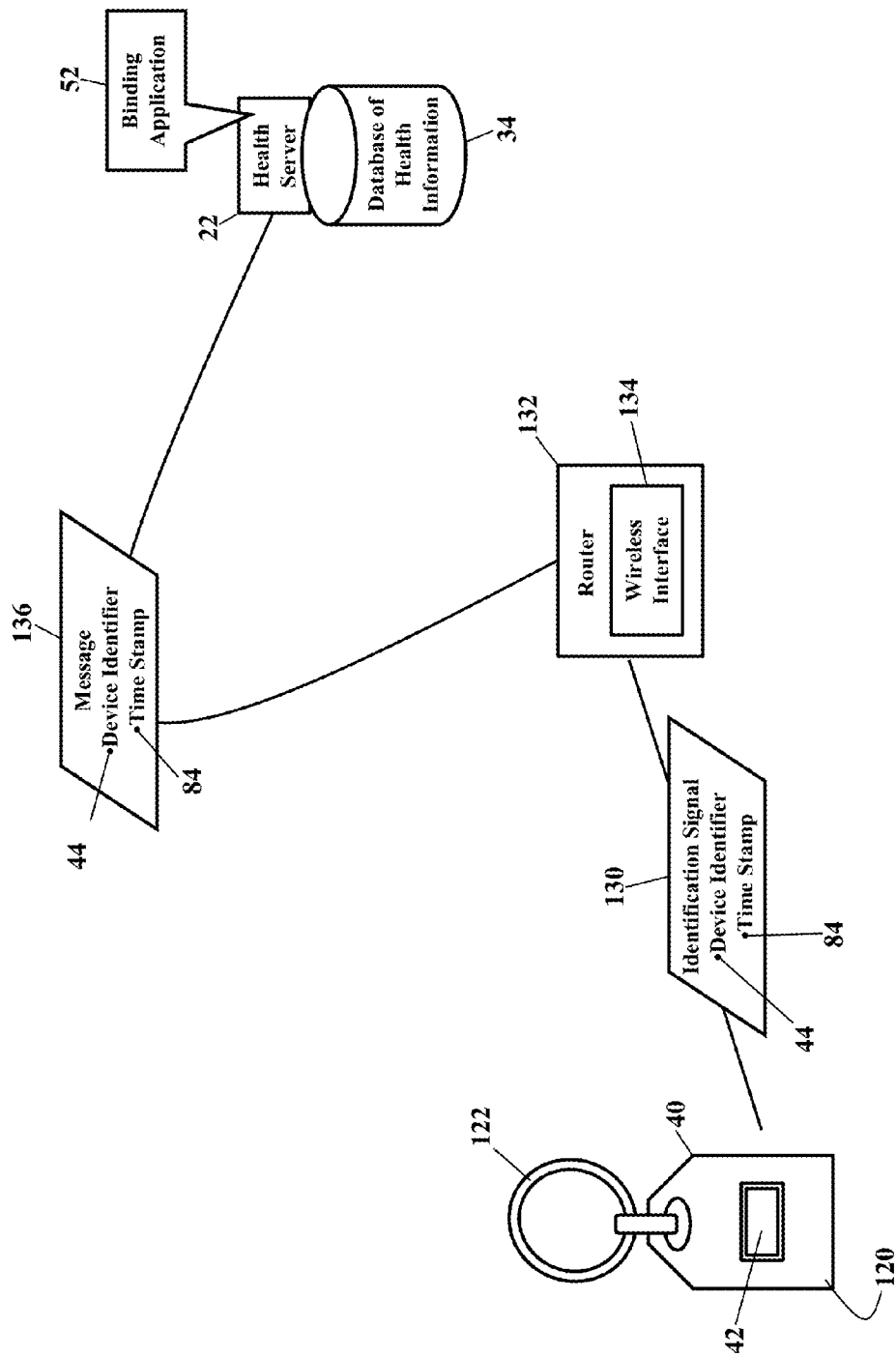

FIG. 6 illustrates a more detailed operating environment for the key fob 120, according to exemplary embodiments. When the user depresses the button 42 on the key fob 120, here the key fob 120 sends an identification signal 130. The identification signal 130 is illustrated as being wirelessly transmitted to a router 132. The router 132 has a wireless interface 134 that receives the identification signal 130. The router 132 then forwards the device identifier 44 in a packetized message 136 to the health server 22 (via the communications network 24 illustrated in FIG. 1). The device identifier 44 uniquely identifies the key fob 120 associated with the user. When the health server 22 receives the device identifier 44, the health server 22 may bind or associate the sensor measurement 32 to the device identifier 44 of the user's key fob 120. The health server 22 may thus store the sensor measurement 32 in the database 34 of health information, and the sensor measurement 32 is associated or mapped to the device identifier 44 of the user's key fob 120.

Figure 7:
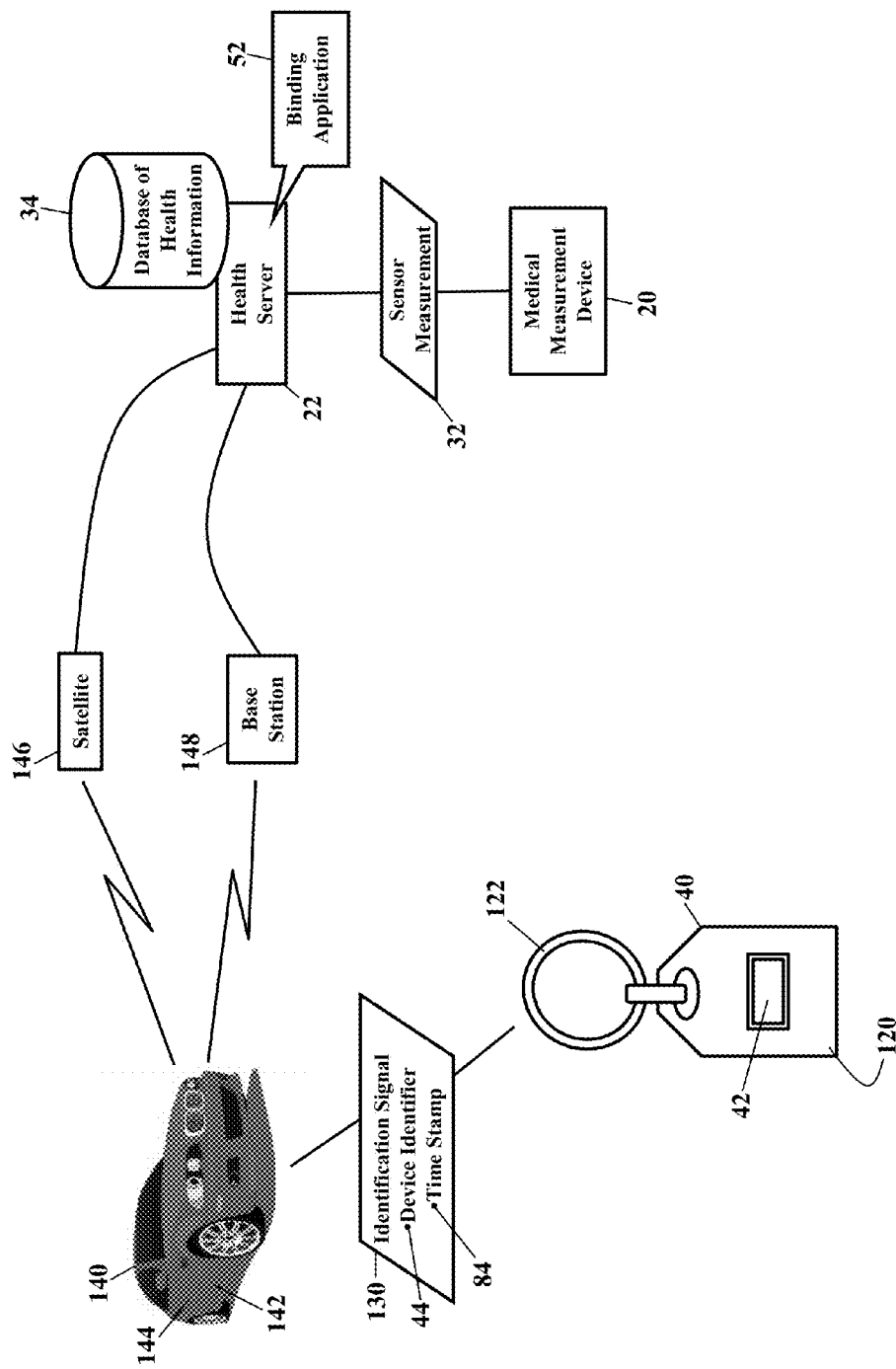

FIG. 7 illustrates an automotive operating environment for the key fob 120, according to exemplary embodiments. As the medical measurement device 20 obtains the sensor measurement 32, the user may depress the button 42 on the key fob 120. Here, though, the key fob 120 communicates with a vehicle 140. The key fob 120 wirelessly sends the identification signal 130, and/or the device identifier 44, to a wireless receiver 142 installed in the vehicle 140. The wireless receiver 142 may operate according to BLUETOOTH, WI-FI, or any other I.E.E.E. 802 family of standards. The wireless receiver 142 may utilize any portion of the electromagnetic spectrum and any signaling standard (such as GSM/CDMA/TDMA or any cellular standard, and/or the ISM band). A transmitter 144 in the vehicle 140 then wirelessly sends the device identifier 44 to a base station 146 or to an orbiting satellite 148. When the base station 146 or the satellite 148 receives the device identifier 44, the base station 146 and the satellite 148 forwards the device identifier 44 to the address associated with the health server 22 (via the communications network 24 illustrated in FIG. 1). The device identifier 44 again uniquely identifies the key fob 120. The health server 22 binds or associates the sensor measurement 32 to the device identifier 44 of the user's key fob 120, as earlier paragraphs explained.

Figure 8:
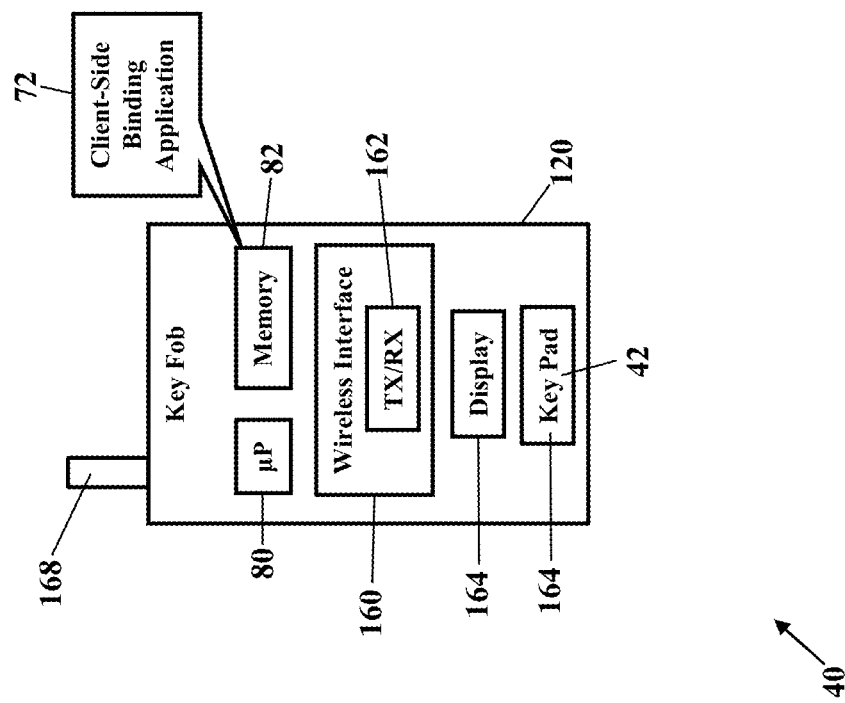

FIG. 8 is a block diagram of the key fob 120, according to exemplary embodiments. The key fob 120 has the processor 80 and the memory 82 and a wireless interface 160. The wireless interface 160 may include a transmitter and/or receiver (illustrated as "TX/RX" 162) for transmitting and/or receiving wireless signals. The wireless interface 160 may operate according to WI-FI, BLUETOOTH, or any of the IEEE 802 family of standards. The wireless interface 160 may utilize any portion of the electromagnetic spectrum and any signaling standard (such as GSM/CDMA/TDMA or any cellular standard, and/or the ISM band). The key fob 120 may even have a display 164. When the user depresses the button 42 on a key pad 166, the transmitter 162 wirelessly sends the device identifier 44 from an antenna 168.

Figure 9:
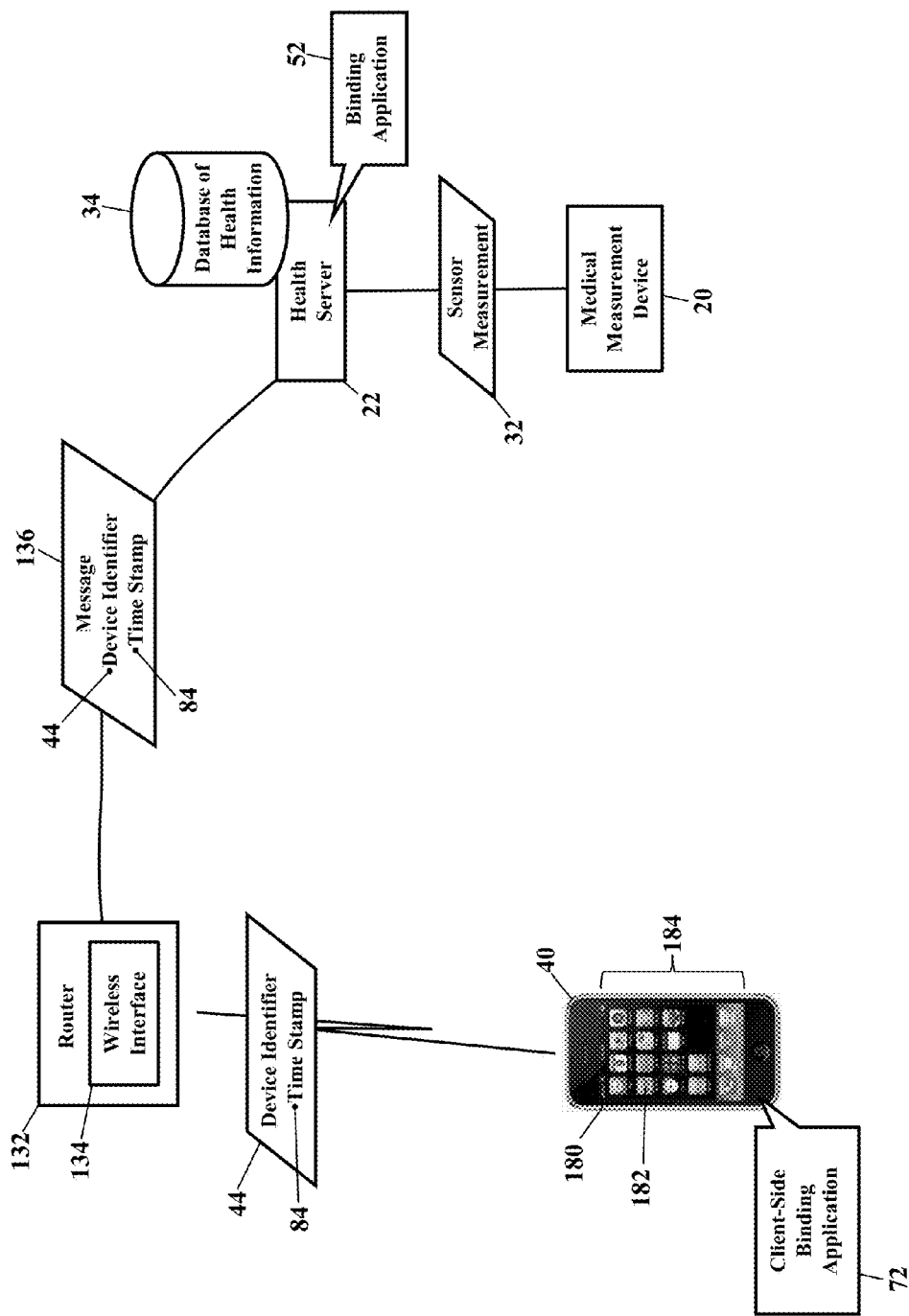
FIG. 9 is a schematic illustrating personal digital assistant, according to exemplary embodiments.

FIG. 9 is a schematic illustrating the user's communications device 40, according to exemplary embodiments. Here the user's communications device 40 is illustrated as a personal digital assistant 180. As the medical measurement device 20 obtains the sensor measurement 32, the user makes an input or selection on the personal digital assistant 180. The personal digital assistant 180 is illustrated as an APPLE® IPHONE® that executes the client-side binding application 72. The personal digital assistant 180, however, may be any other manufacturer's model. The user, for example, may touch an icon 182 on a display 184. The personal digital assistant 180 then wirelessly sends the device identifier 44. FIG. 9 illustrates wireless transmission to the wireless interface 134 of the router 132. The router 132 then forwards the device identifier 44 in the packetized message 136 to the health server 22. The health server 22 then binds or associates the sensor measurement 32 to the device identifier 44 associated with the personal digital assistant 180.

Figure 10:
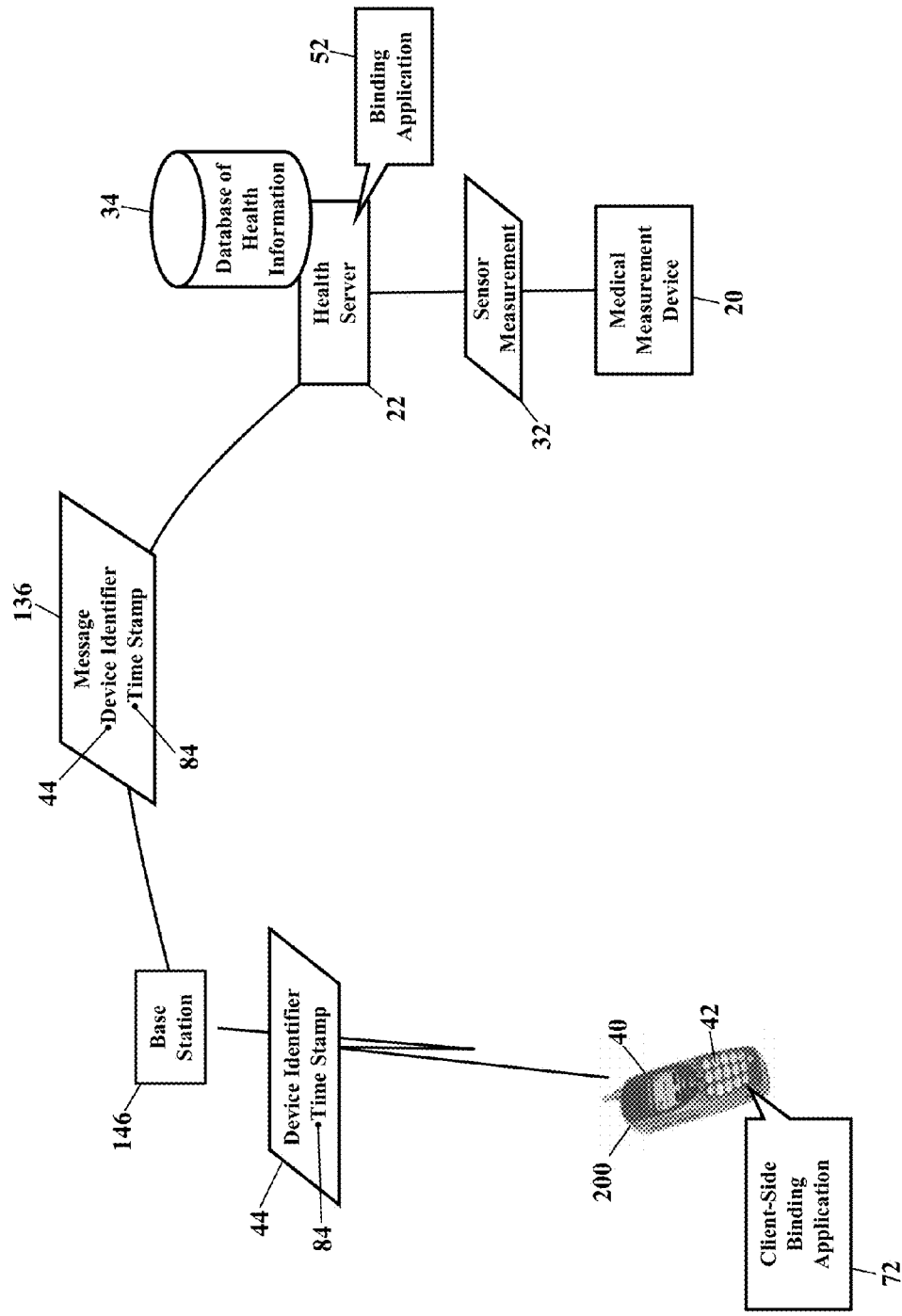
FIG. 10 is schematic illustrating a cellular phone, according to exemplary embodiments.

FIG. 10 is another schematic illustrating the user's communications device 40, according to exemplary embodiments. Here the user's communications device 40 is illustrated as a cellular phone 200. As the medical measurement device 20 obtains the sensor measurement 32, the user makes an input or selection on the cellular phone 200 (such as by pushing the button 42). The cellular phone 200 executes the client-side binding application 72 and wirelessly sends the device identifier 44 to the base station 146. The base station 146 then forwards the device identifier 44 in the packetized message 136 to the address associated with the health server 22. The health server 22 then binds or associates the sensor measurement 32 to the device identifier 44 associated with the personal digital assistant 180.

Figure 11:
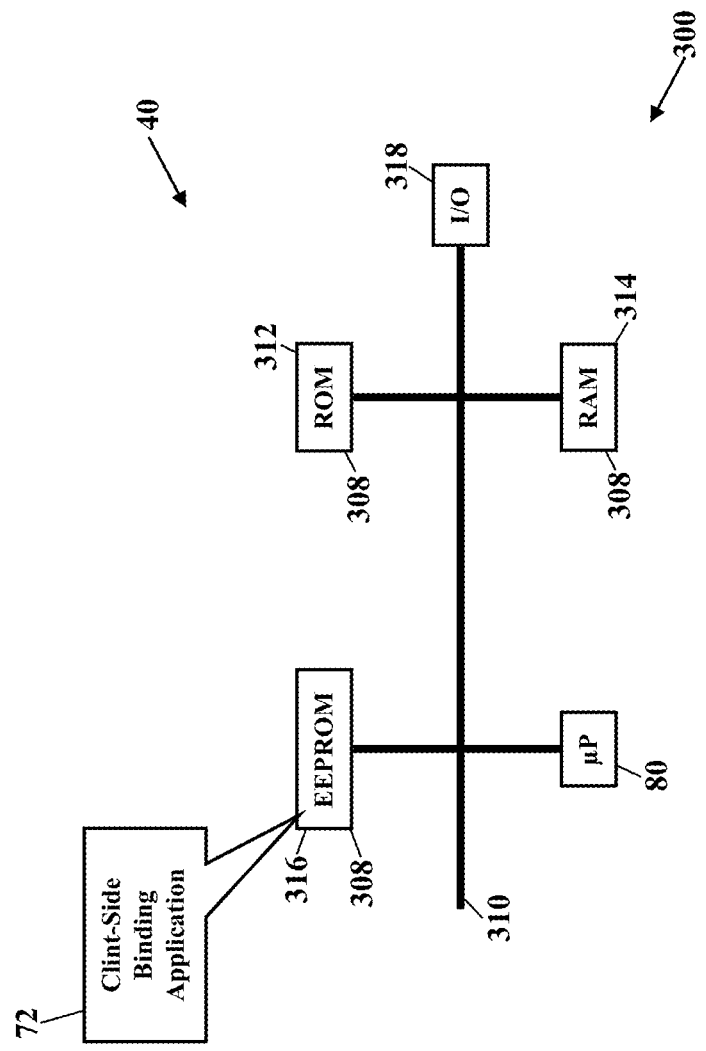
FIGS. 11-14 are schematics a communications device, according to exemplary embodiments.
Figure 13:
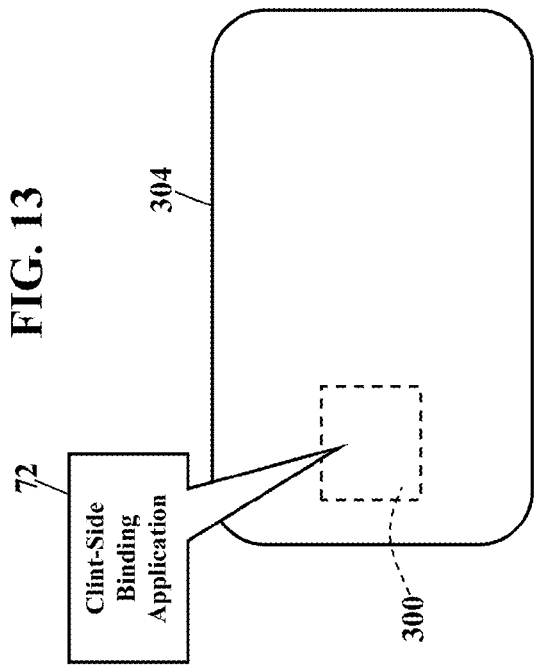
Figure 12:
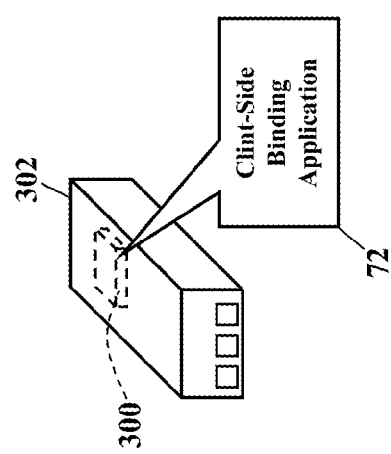

FIGS. 11-13 are schematics further illustrating the user's communications device 40, according to exemplary embodiments. FIG. 11 is a block diagram of a Subscriber Identity Module 300, while FIGS. 12 and 13 illustrate, respectively, the Subscriber Identity Module 300 embodied in a plug 302 and in a card 304. As those of ordinary skill in the art recognize, the Subscriber Identity Module 300 may be used in conjunction with many communications devices (such as the personal digital assistant 180 and the cellular phone 200, illustrated respectively in FIGS. 9 and 10). The Subscriber Identity Module 300 stores user information (such as the user's International Mobile Subscriber Identity, the user's $K_i$ number, and other user information) and any portion of the client-side binding application 72. As those of ordinary skill in the art also recognize, the plug 302 and the card 304 each interface with the communications device 40.

FIG. 11 is a block diagram of the Subscriber Identity Module 300, whether embodied as the plug 302 of FIG. 12 or as the card 304 of FIG. 13. Here the Subscriber Identity Module 300 comprises the processor (μP) 80 communicating with memory modules 308 via a data bus 310. The memory modules 308 may include Read Only Memory (ROM) 312, Random Access Memory (RAM) and or flash memory 314, and Electrically Erasable-Programmable Read Only Memory (EEPROM) 316. The Subscriber Identity Module 300 stores some or all of the client-side binding application 72 in one or more of the memory modules 308. FIG. 11 shows the client-side binding application 72 residing in the Erasable-Programmable Read Only Memory 316, yet the client-side binding application 72 may alternatively or additionally reside in the Read Only Memory 312 and/or in the Random Access/Flash Memory 314. An Input/Output module 318 handles communication between the Subscriber Identity Module 300 and the communications device 40. Because Subscriber Identity Modules are well known in the art, this disclosure will not further discuss the operation and the physical/memory structure of the Subscriber Identity Module 300.

Figure 14:
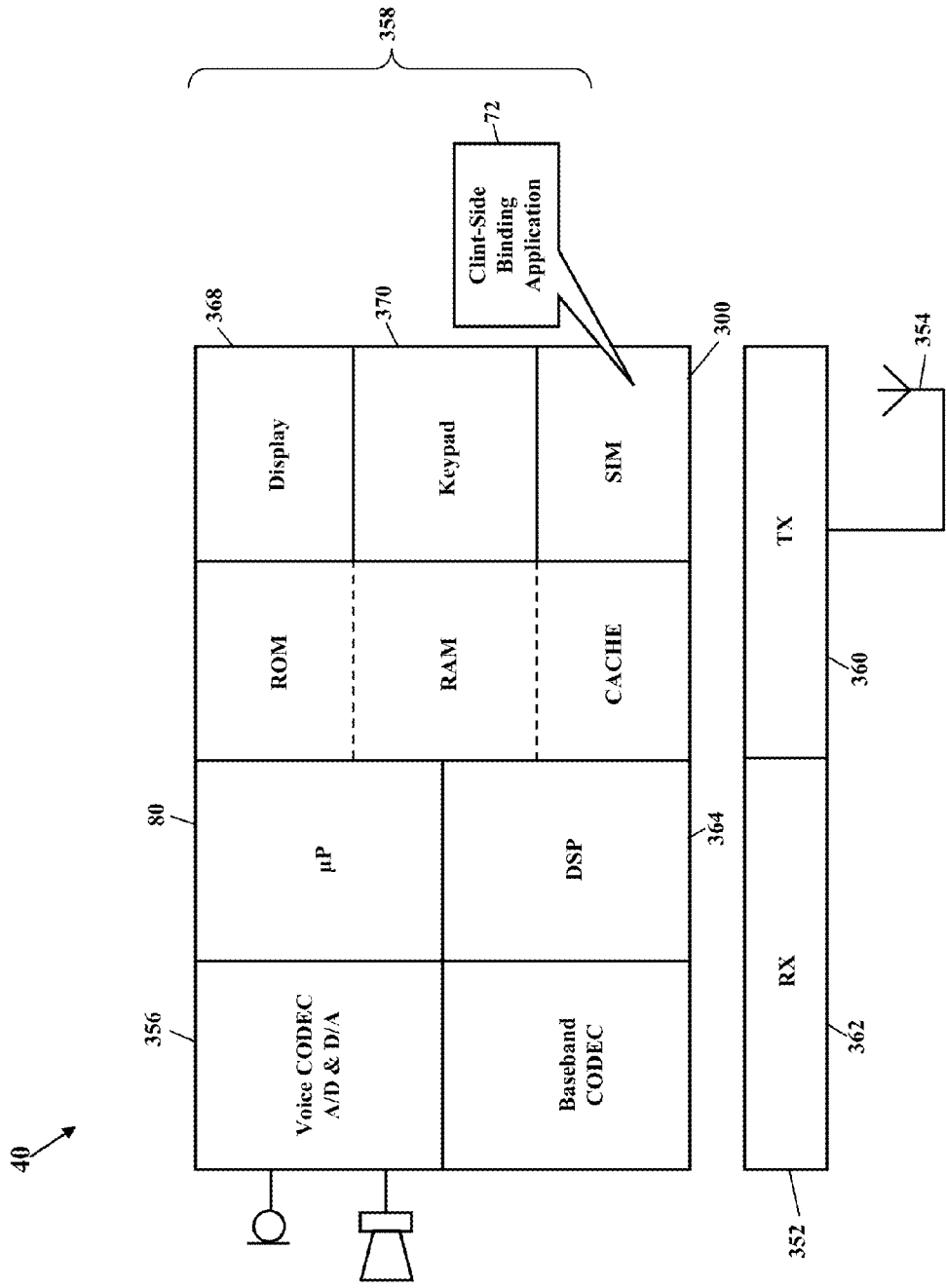

FIG. 14 is another schematic illustrating the communications device 40, according to exemplary embodiments. Here the communications device 40 comprises a radio transceiver unit 352, an antenna 354, a digital baseband chipset 356, and a man/machine interface (MMI) 358. The transceiver unit 352 includes transmitter circuitry 360 and receiver circuitry 362 for receiving and transmitting radio-frequency (RF) signals. The transceiver unit 352 couples to the antenna 354 for converting electrical current to and from electromagnetic waves. The digital baseband chipset 356 contains a digital signal processor (DSP) 364 and performs signal processing functions for audio (voice) signals and RF signals. As FIG. 14 shows, the digital baseband chipset 356 may also include the on-board microprocessor 80 that interacts with the man/machine interface (MMI) 358. The man/machine interface (MMI) 358 may comprise a display device 368, a keypad 370, and the Subscriber Identity Module 300. The on-board microprocessor 80 may perform TDMA, CDMA, GSM or other protocol functions and control functions for the radio circuitry 360 and 362, for the display device 368, and for the keypad 370. The on-board microprocessor 80 may also interface with the Subscriber Identity Module 300 and with the client-side binding application 72. Because the functional architecture of the communications device 40 is well known to those of ordinary skill in the art, the architecture will not be further discussed.

Exemplary embodiments may be applied to any signaling standard. As those of ordinary skill in the art recognize, FIGS. 11-14 may illustrate a Global System for Mobile (GSM) communications device. That is, the communications device 40 may utilize the Global System for Mobile (GSM) communications signaling standard. Those of ordinary skill in the art, however, also recognize that exemplary embodiments are equally applicable to any communications device 40 utilizing the Time Division Multiple Access signaling standard, the Code Division Multiple Access signaling standard, the "dual-mode" GSM-ANSI Interoperability Team (GAIT) signaling standard, or any variant of the GSM/CDMA/TDMA signaling standard. Exemplary embodiments may also be applied to other standards, such as the I.E.E.E. 802 family of standards, the Industrial, Scientific, and Medical band of the electromagnetic spectrum, BLUETOOTH®, and any other.

Figure 15:
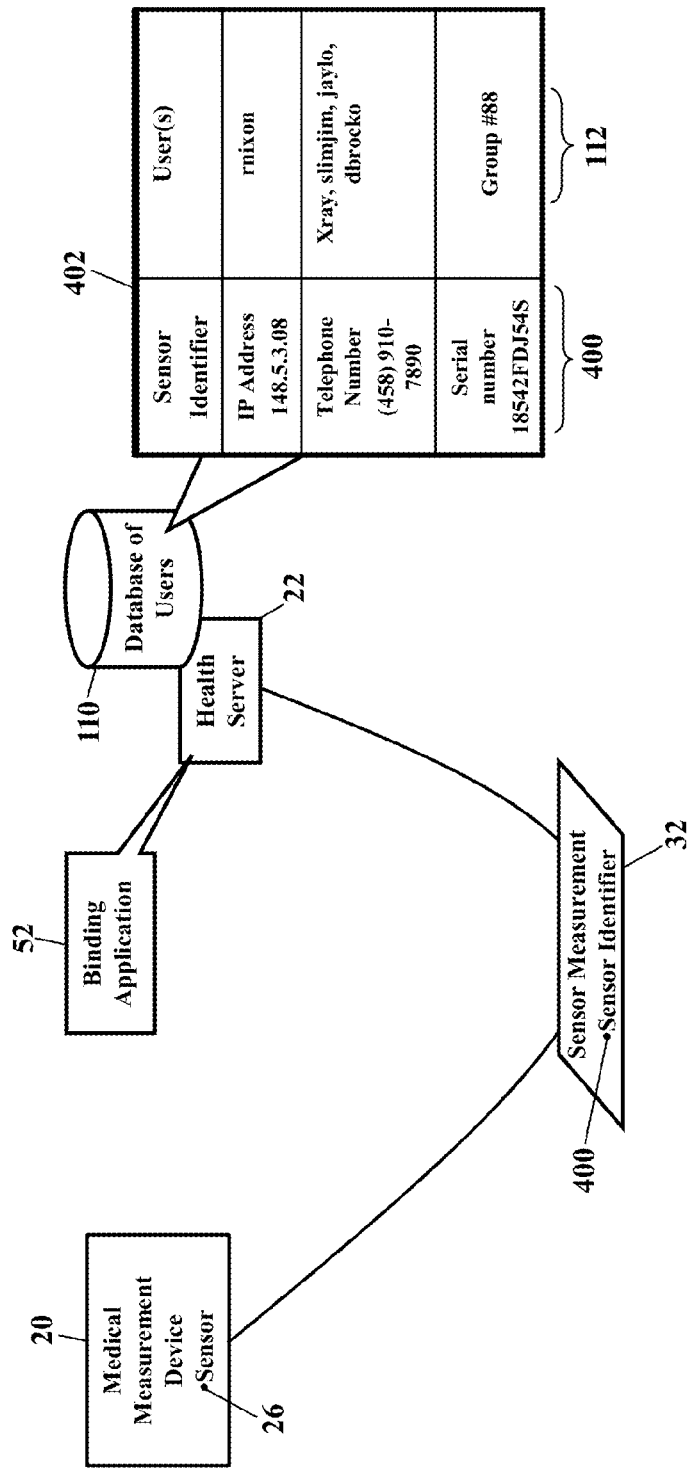
FIG. 15 is a schematic illustrating a sensor identifier, according to exemplary embodiments.

FIG. 15 is a schematic illustrating a sensor identifier 400, according to exemplary embodiments. When the health server 22 receives the sensor measurement 32 from the medical measurement device 20, the sensor measurement 32 may include the sensor identifier 400. The sensor identifier 400 uniquely identifies the medical measurement device 20, and/or the sensor 26, that sent the sensor measurement 32. The sensor identifier 400 may be a serial number, Internet Protocol address, telephone number, or any other alphanumeric combination. When the health server 22 receives the sensor identifier 400, the binding application 52 may use the sensor identifier 400 to further help identify the user of the medical measurement device 20.

The binding application 52 may then query the database 110 of users. Here the database 110 of users also stores associations between sensor identifiers 400 and users 112. Once the sensor identifier 400 is known, the database 110 of users may reveal a single user, or a group of users, that are associated with the sensor identifier 400. The binding application 52 queries the database 110 of users for the sensor identifier 400 and retrieves the associated user or group of users. Many medical measurement devices are shared by multiple users (as earlier paragraphs explained). The database 110 of users is illustrated as a table 402 that maps, relates, or otherwise associates the sensor identifier 400 to one or more users 112. The binding application 52 queries the database 110 of users for the sensor identifier 400 and retrieves the single user, or a group of users, that is/are associated with the sensor identifier 400.

Figure 16:
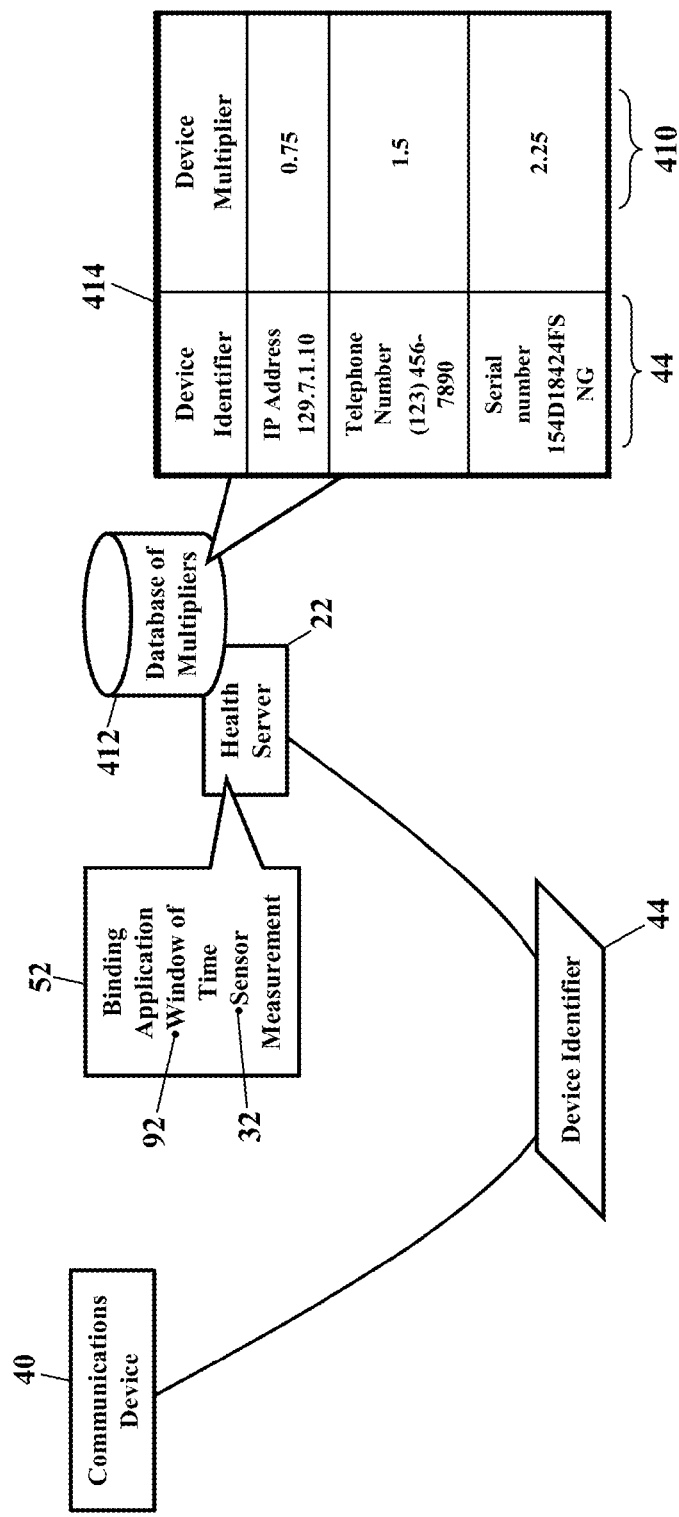
FIG. 16 is a detailed schematic illustrating multipliers, according to exemplary embodiments.

FIG. 16 is another detailed schematic illustrating multipliers, according to exemplary embodiments. Here multipliers may be used to expand, or contract, the window 92 of time. FIG. 16, for example, illustrates a device multiplier 410 that may be associated to the device identifier 44, according to exemplary embodiments. The device multiplier 410 may be a multiplication factor that increases, or decreases, the window 92 of time. The window 92 of time, in other words, may be increased, or decreased, based on the communications device 40 that sent the device identifier 44. Suppose, for example, that the device identifier 44 reveals that the user's communications device 40 has a large form-factor keypad. The keys of the keypad are enlarged for easier identification and depression. These enlarged keys may indicate that the user has reduced eyesight or physical capabilities. The device multiplier 410, then, may be used to expand the window 92 of time. If the device identifier 44 indicates that the user may need additional time to perfect the binding, then the window 92 of time may be adjusted to provide more time.

The binding application 52 may thus query a database 412 of multipliers. The database 412 of multipliers stores associations between device identifiers 44 and device multipliers 410. Once the device identifier 44 is known, the database 412 of multipliers may be queried for the corresponding device multiplier 410. The database 412 of multipliers is illustrated as being locally stored in the health server 22, but the database 412 of multipliers may be remotely accessed. The database 412 of multipliers is illustrated as a table 414 that maps, relates, or otherwise associates the device identifier 44 to the corresponding device multiplier 410. The binding application 52 queries the database 412 of multipliers for the device identifier 44 and retrieves the corresponding device multiplier 410. The binding application 52 may then increase, or decrease, the window 92 of time based on the device multiplier 410. If the window 92 of time is one minute (60 seconds), for example, and the device multiplier 410 is 1.5, then the final window 92 of time is (60 seconds)×(1.5)=90 seconds.

Conversely, should the device identifier 44 indicate that the communications device 40 is an APPLE® IPHONE® or other "smart" device, then the user may be proficient and skilled at binding their sensor measurement 32 to the input to their communications device 40. In this case, then, the device multiplier 410 may actually reduce the window 92 of time. Again, if the window 92 of time is one minute (60 seconds), but the device multiplier 410 is 0.75, then the final window 92 of time is (60 seconds)×(0.75)=45 seconds.

Figure 17:
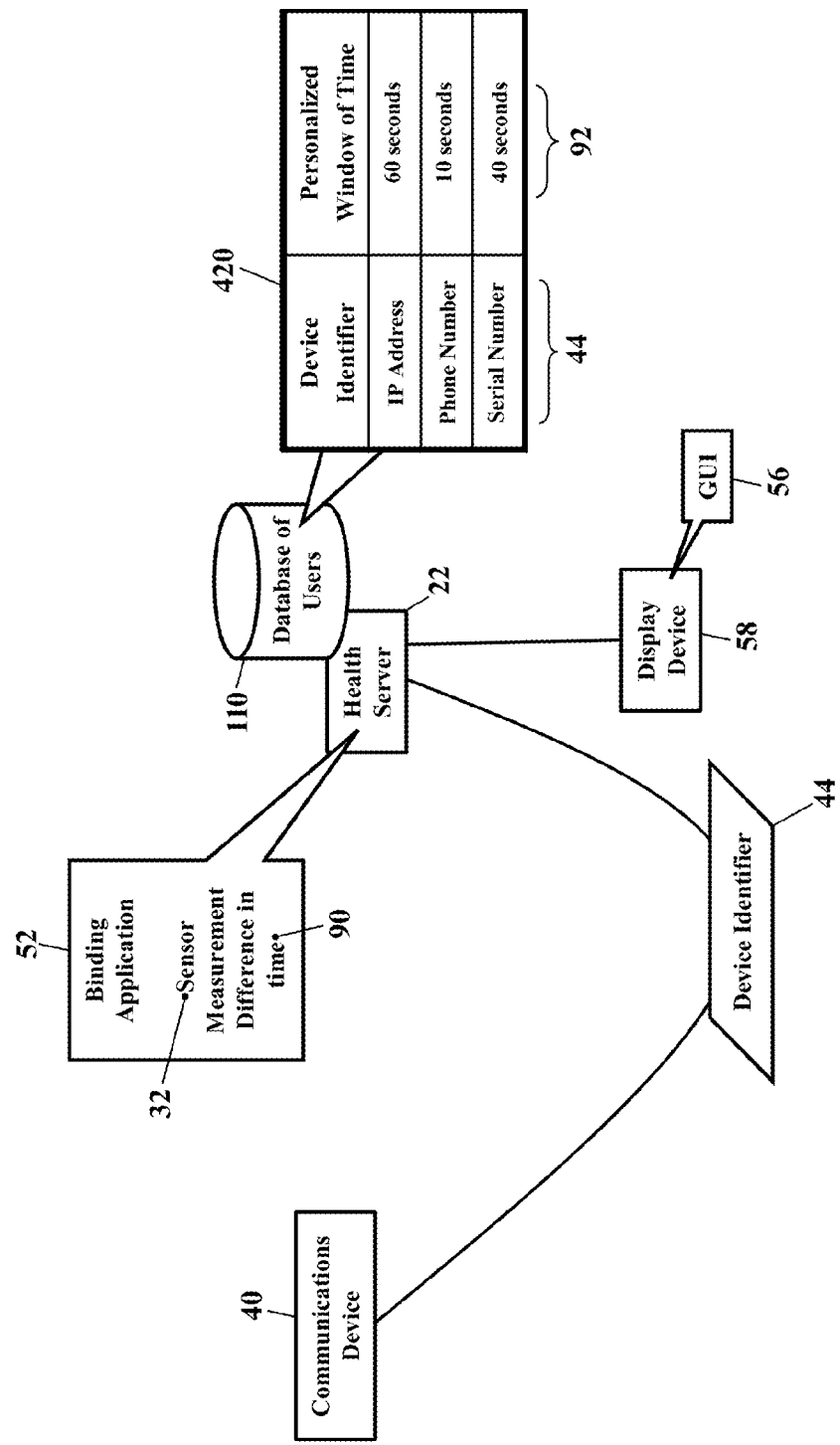
FIGS. 17-18 are schematics illustrating personalized windows of time, according to exemplary embodiments.

FIG. 17 is a schematic illustrating personalized windows of time, according to exemplary embodiments. Here each individual user may determine and configure a unique window 92 of time. The window 92 of time, in other words, may be associated with the device identifier 44. Exemplary embodiments may thus permit each user to configure and personalize the window 92 of time, based on the user's individual characteristics or capabilities. If the user is proficient, then the user may want a short window 92 of time. If a different user desires more time to perfect the binding, then the window 92 of time may be longer for that user. The window 92 of time may thus be configurable to suit each user's desires.

FIG. 17 further illustrates the database 110 of users. The database 110 of users stores associations between device identifiers and windows of time. Once the device identifier 44 is obtained, the database 110 of users may be queried for the corresponding window 92 of time. The database 110 of users is illustrated as being locally stored in the health server 22, but the database 110 of users may be remotely accessed. The database 110 of users is illustrated as a table 420 that maps, relates, or otherwise associates the device identifier 44 to the corresponding window 92 of time. The binding application 52 queries the database 110 of users for the device identifier 44 and retrieves the corresponding window 92 of time. The binding application 52 may then use the window 92 of time when comparing the difference 90 in time between the sensor measurement 32 and the corresponding window 92 of time (as earlier paragraphs explained).

The graphical user interface 56 may be used to input the personalized window 92 of time. The graphical user interface 56 may include one or more visual and/or audible prompts for personalizing the window 92 of time. The graphical user interface 56 may include one or more data fields for entry of a user's personalized window 92 of time. Once a user inputs their desired window 92 of time, then the user's personalized window 92 of time may be stored and associated to the device identifier 44 in the database 110 of users.

Figure 18:
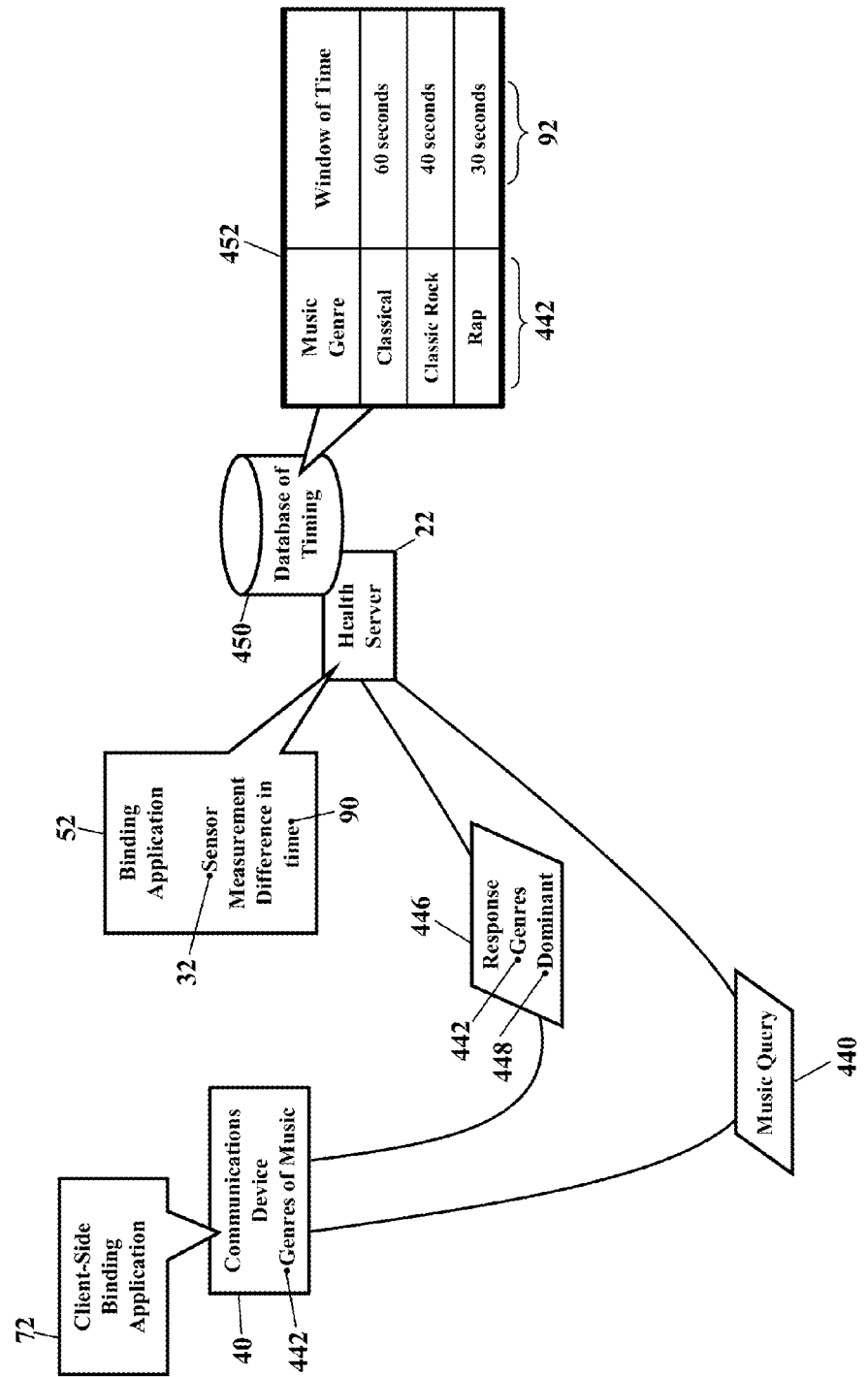

FIG. 18 is another schematic illustrating personalized windows of time, according to exemplary embodiments. Here the window 92 of time may also be determined from a user's music selections. The binding application 52 may query the user's communications device 40 for genres of music stored and/or played by the communications device 40. The age of the user may be inferred from the genres of music, and the length of the window 92 of time may then be adjusted based on the user's age. The window 92 of time, in other words, may be at least partially derived from the genres of music enjoyed by the user. Rap music may indicate a younger and more proficient user, so the window 92 of time may be reduced (perhaps to a minimum value). Classic rock may indicate a member of the "baby boomer" generation, so the window 92 of time may be increased to a middle value. 1940s and 1950s music may indicate seniors and elderly, so the window 92 of time may be expanded to a maximum value. The window 92 of time may be further refined by "decades" music, such as 70s, 80s, and 90s hits that may more accurately indicate the user's age.

FIG. 18 thus illustrates a music query 440. When the health server 22 communicates with the user's communications device 40, the binding application 52 may communicate with the client-side binding application 72 stored in the user's communications device 40. The binding application 52 and the client-side binding application 72 cooperate to determine the genres 442 of music that are stored by, and/or played by, the communications device 40. The binding application 52 causes the processor in the health server 22 to send the music query 440. The music query 440 communicates to an address associated with the user's communications device 40. When the user's communications device 40 receives the music query 440, the client-side binding application 52 causes the client processor (illustrated as reference numeral 80 in FIG. 2) in the user's communications device 40 to determine the genres 442 of music stored and/or played by the communications device 40. If the user's communications device 40 stores or plays multiple genres, then the client-side binding application 52 may determine which genre is most played or enjoyed in time. The client-side binding application 52, for example, may determine that "90s hits" are cumulatively played or executed more than any other genre.

The client-side binding application 52 may send a response 446. The response 446 may include information related to the genres 442 of music stored and/or played by the communications device 40. More particularly, the response 446 may identify a dominant genre 448 achieving the most playing time. When the health server 22 receives the response 446, the binding application 52 retrieves the genres 442 of music stored and/or played by the communications device 40 and/or the dominant genre 448 having the greatest cumulative playing time.

The binding application 52 may then consult a database 450 of timing. The database 450 of timing information stores associations between the genres 442 of music and the window 92 of time. Once the user's music selections are identified, the database 450 of timing information may be queried for the corresponding window 92 of time. The database 450 of timing information is illustrated as being locally stored in the health server 22, but the database 450 of timing information may be remotely accessed. The database 450 of timing information is illustrated as a table 452 that maps, relates, or otherwise associates the genres 442 of music to the corresponding window 92 of time. The binding application 52 queries the database 450 of timing information for the genres 442 of music and retrieves the corresponding window 92 of time. The binding application 52 may then use the window 92 of time when comparing the difference 90 in time between the sensor measurement 32 and the corresponding window 92 of time (as earlier paragraphs explained).

Few users, though, have a single genre of music in their music selection. Most users have many genres of music, and each genre is enjoyed at different times. The binding application 52, then, may blend windows of time when multiple genres of music are identified. This blending may correspond to the cumulative times for each genre of music. Again referring to FIG. 18, suppose classical music is dominate and enjoyed 60% of the total playing time, while classic rock is 20% and rap is 20%. The binding application 52, then, may blend their windows 92 of time to obtain a final value for the window 92 of time according to $$\text{final window of time} = [(0.6) \times (60 \text{ seconds})] + [(0.2) \times (40 \text{ seconds})] + [(0.2) \times (40 \text{ seconds})],$$

or $$\text{final window of time} = 52 \text{ seconds}.$$

Here, then, the final value for the window 92 of time is proportional to the cumulative playing time for each genre of music. The binding application 52 may then use the final value (e.g., 52 seconds) for the window 92 of time when comparing the difference 90 in time between the sensor measurement 32 and the corresponding window 92 of time (as earlier paragraphs explained).

Figure 19:
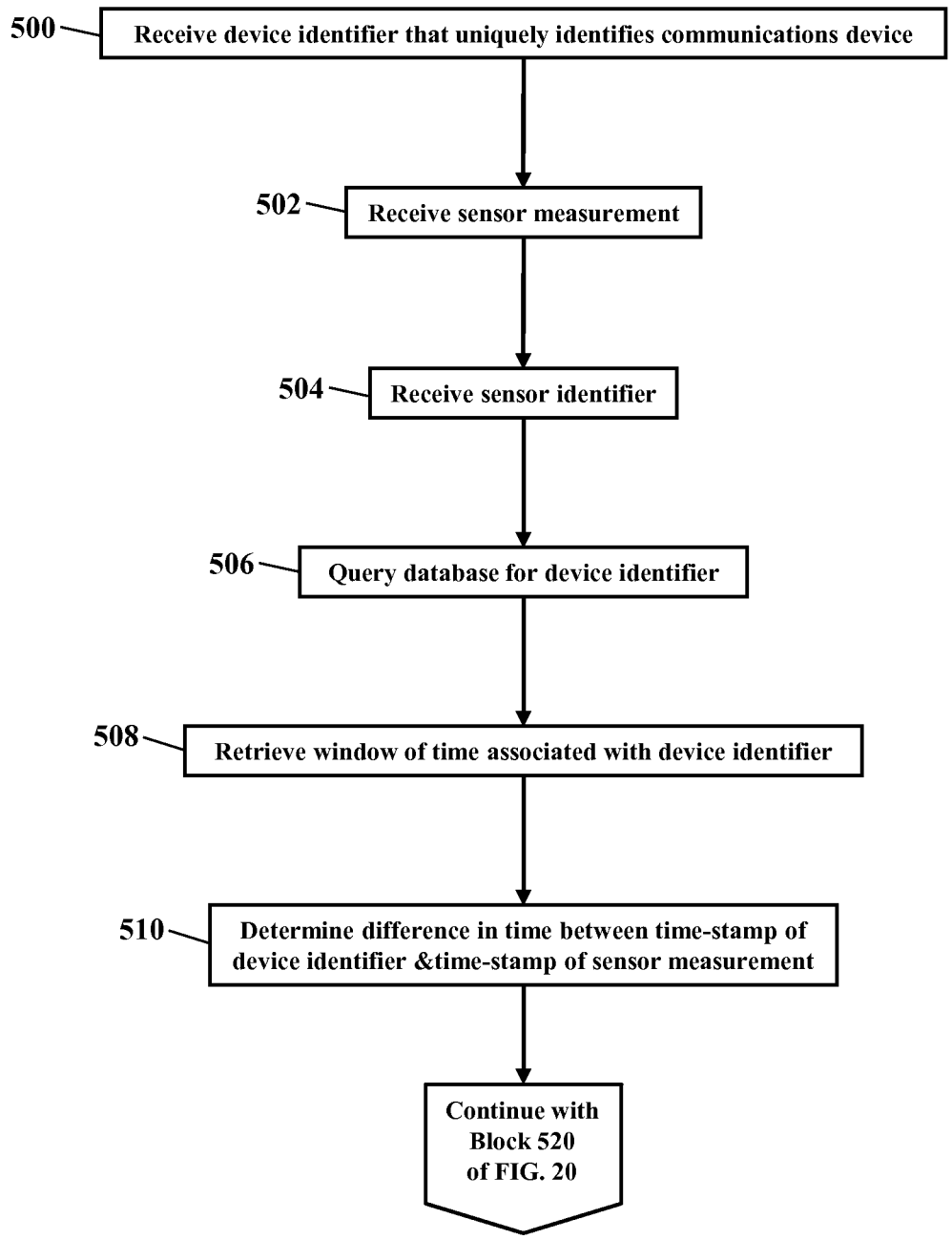
FIGS. 19-20 are flowcharts illustrating a method of measuring health, according to exemplary embodiments.
Figure 20:
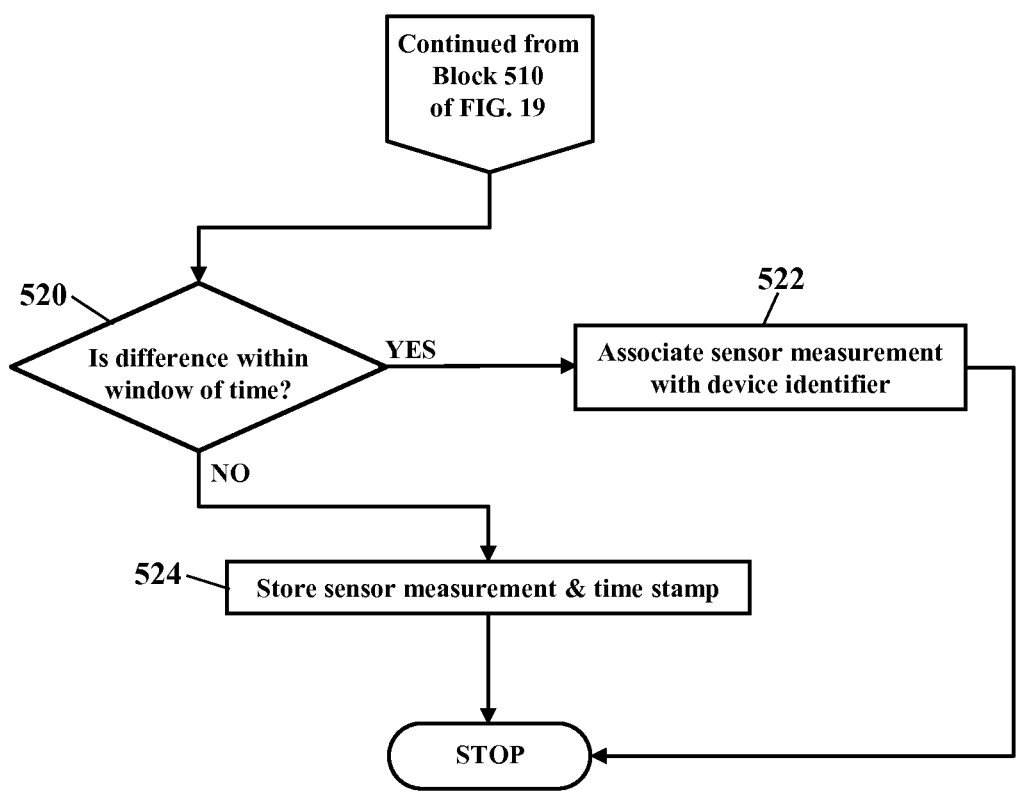

FIGS. 19-20 are flowcharts illustrating a method of measuring health, according to exemplary embodiments. A device identifier is received that uniquely identifies a communications device (Block 500). A sensor measurement is received (Block 502). A sensor identifier, associated with a sensor that measured the sensor measurement, is received (Block 504). A database is queried for the device identifier (Block 506) and a window of time is retrieved (Block 508). A difference in time is determined between a time-stamp of the device identifier and a time-stamp of the sensor measurement (Block 510).

The flowchart continues with FIG. 20. If the difference in time is within the window of time (Block 520), then the sensor measurement is associated with the device identifier (Block 522). If the difference in time is outside the window of time (Block 520), then the sensor measurement cannot be bound without further information, so the sensor measurement is stored in a database, along with the associated time stamp (Block 524).

Figure 21:
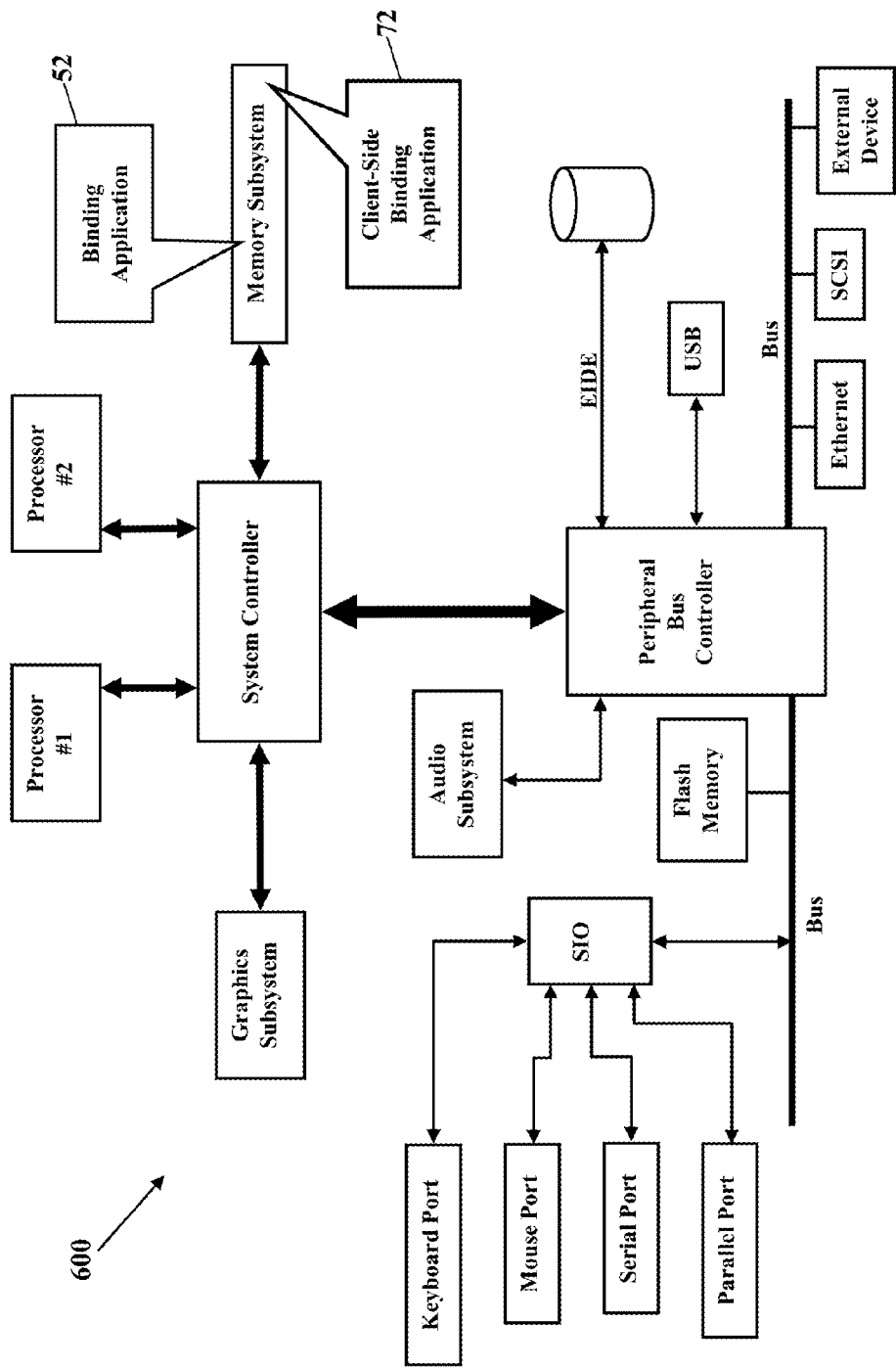
FIG. 21 is a schematic illustrating a processor-controlled device, according to exemplary embodiments.

FIG. 21 is a schematic illustrating still more exemplary embodiments. FIG. 21 is a generic block diagram illustrating the binding application 52 operating within a processor-controlled device 600. FIGS. 1-10 illustrated the binding application 52 operating within the health server 22. As explained, though, the binding application 52 may operate in any processor-controlled device 600. FIG. 21, then, illustrates the binding application 52 stored in a memory subsystem of the processor-controlled device 600. FIG. 21 also illustrates the client-side binding application 72 operating within the processor-controlled device 600. The medical measurement device 20 and the communications device 40, in other words, may be any processor-controlled device 600. One or more processors communicate with the memory subsystem and execute the binding application 52 and/or the client-side binding application 72. Because the processor-controlled device 600 is well-known to those of ordinary skill in the art, no detailed explanation is needed.

Figure 22:
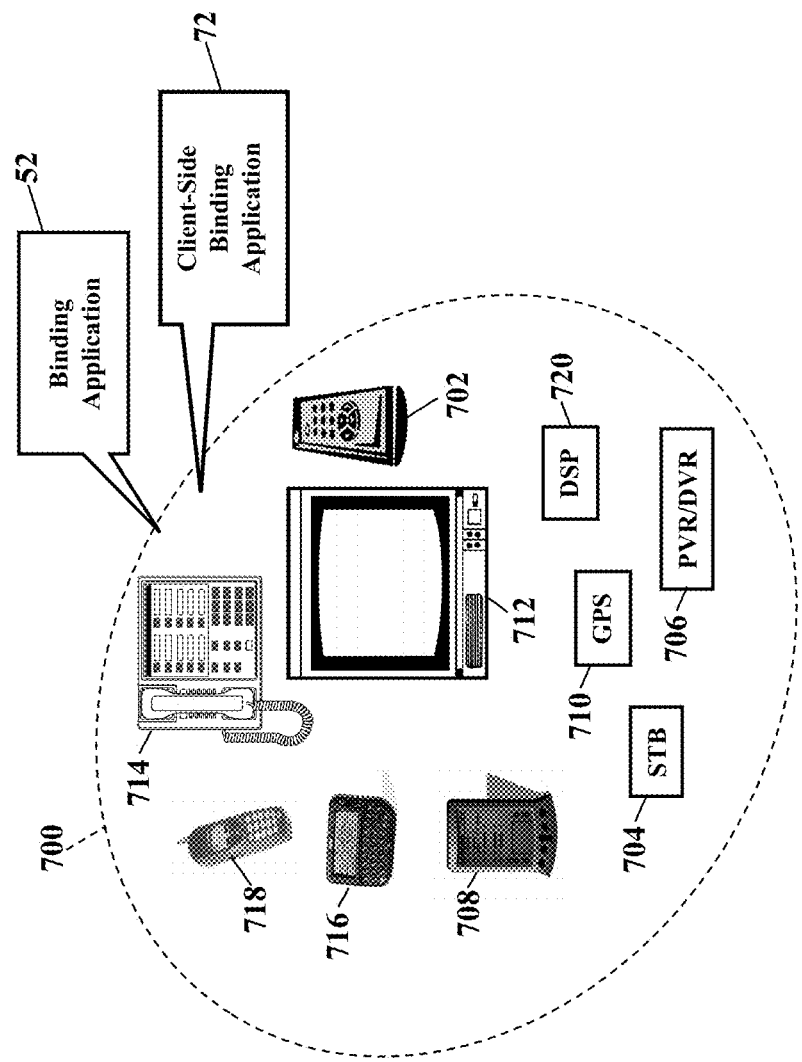
FIG. 22 depicts other possible operating environments for additional aspects of the exemplary embodiments.

FIG. 22 depicts other possible operating environments for additional aspects of the exemplary embodiments. FIG. 22 illustrates the binding application 52 and the client-side binding application 72 operating within various other devices 700. FIG. 22, for example, illustrates that the binding application 52 and/or the client-side binding application 72 may entirely or partially operate within a remote control 702, a set-top box ("STB") (704), a personal/digital video recorder (PVR/DVR) 706, a personal digital assistant (PDA) 708, a Global Positioning System (GPS) device 710, an interactive television 712, an Internet Protocol (IP) phone 714, a pager 716, a cellular/satellite phone 718, or any computer system, communications device, or processor-controlled device utilizing the processor 50 and/or a digital signal processor (DP/DSP) 720. The device 700 may also include watches, radios, vehicle electronics, clocks, printers, gateways, mobile/implantable medical devices, and other apparatuses and systems. Because the architecture and operating principles of the various devices 700 are well known, the hardware and software componentry of the various devices 700 are not further shown and described.

Figure 23:
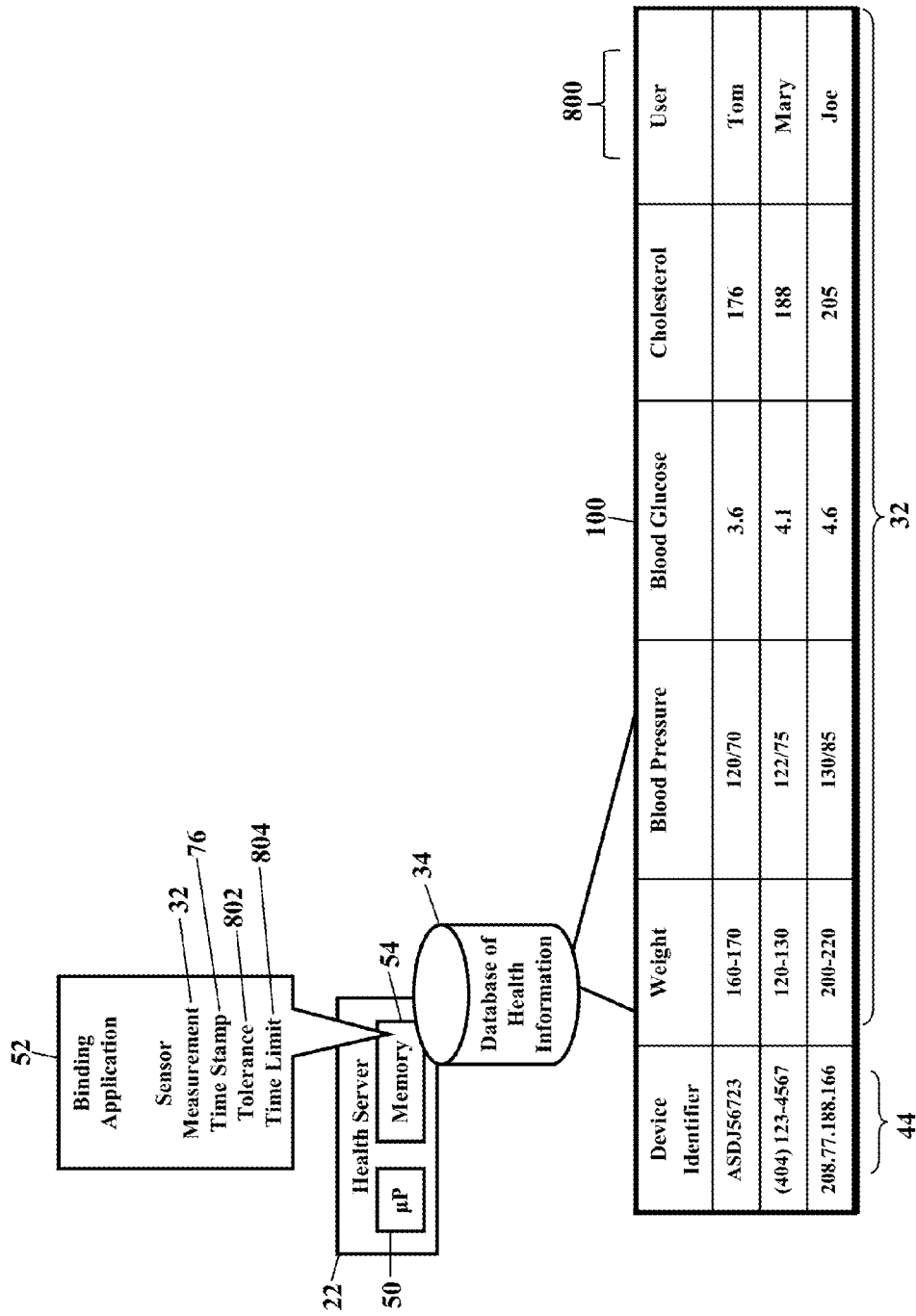
FIGS. 23-29 are schematics illustrating user binding, according to still more exemplary embodiments.

FIGS. 23-26 are schematics further illustrating user binding, according to still more exemplary embodiments. FIG. 23 illustrates how the sensor measurement 32 may be used to identify the user of medical measurement device 20. When the health server 22 receives the sensor measurement 32, the binding application 52 may infer the user from the sensor measurement 32. The binding application 52 may query the database 34 of health information for the sensor measurement 32. Here the database 34 of health information may associate sensor measurements to different users. Even though the medical measurement device 20 may be shared by multiple users, it may be unlikely that the multiple users have similar physiological data (illustrated as reference numeral 28). The multiple users, in other words, are unlikely to share similar weight readings, blood pressure readings, glucose readings, or other physiological data. The binding application 52, then, may infer the user from the sensor measurement 32.

As FIG. 23 illustrates, the database 34 of health information may associate the sensor measurements 32 to different users 800. When the health server 22 receives the sensor measurement 32, the binding application 52 may query the database 34 of health information for the sensor measurement 32. The binding application 52 retrieves the user 800 that matches the sensor measurement 32. The binding application 52 may even apply a tolerance 802 to the sensor measurement 32 to account for permissible fluctuations in readings. Suppose, for example, that the sensor measurement 32 represents a weight reading of 165 pounds. The binding application 52 may query the database 34 of health information for any weight reading of 165 pounds. The binding application 52 the retrieves the user 800 that has a database entry matching 165 pounds. The binding application 52 may even apply the tolerance 802 of ±5 pounds and broaden the query to 160-170 pounds. The binding application 52 thus retrieves the user 800 that has a previous weight reading in the range of 160-170 pounds.

The binding application 52 may even apply a time limit 804 to further limit the query. When the binding application 52 queries for the user 800 associated with the sensor measurement 32, the time limit 804 may constrain the query to only recent database entries. Suppose, for example, that a database entry matches the range of 160-170 pounds, but the database entry is two years old. The database entry is obviously old and stale and may not correctly associate to the correct user of the medical measurement device 20. The time limit 804, then, may limit the query to only fresh or recent entries. The time limit 804 may thus be configured to a maximum-permissible hourly or daily limit on a date/time of the entries in the database 34 of health information. When the binding application 52 obtains a matching database entry to the sensor measurement 32, the binding application 52 may compare a data/time associated with the database entry to the time limit 804. If the date/time associated with the database entry exceeds, or is older than, the time stamp 76, then the binding application 52 may disregard the query result as stale. The binding application 52, in other words, cannot confidently match the sensor measurement 32 (received from the medical measurement device 20) to a user in the database 34 of health information. When, however, the date/time associated with the database entry is within the time limit 804, then the binding application 52 may confidently match the sensor measurement 32 to a user in the database 34 of health information.

Figure 24:
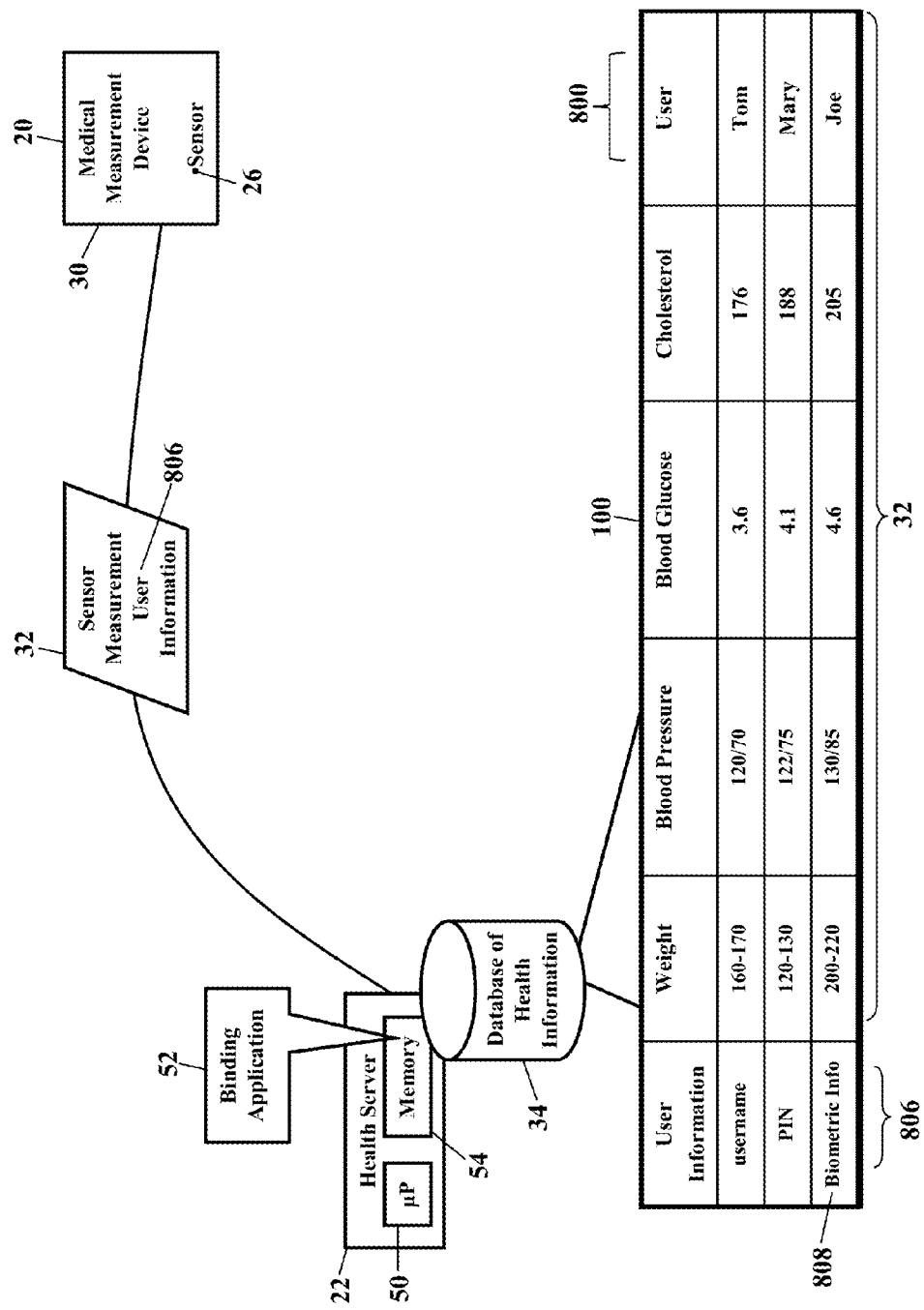

FIG. 24 illustrates user information 806, according to more exemplary embodiments. Here the user information 806 may be used to identify the user of medical measurement device 20. When the health server 22 receives the sensor measurement 32, the sensor measurement 32 may include the user information 806. The user information 806 may be any information that can be collected at and/or by the medical measurement device 20. The user information 806, for example, may be a username or personal identification number ("PIN") entered into a user interface of the medical measurement device 20. If the medical measurement device 20 includes a keypad or touch screen, then the user may enter their unique user information 806. The medical measurement device 20 may then send the user information 806 with the sensor measurement 32. When the health server 22 receives the user information 806, the binding application 52 may use the user information 806 to determine or infer the user of the medical measurement device 20.

The user information 806 may include biometric information 808. When the medical measurement device 20 obtains the sensor measurement 32, the medical measurement device 20 may also obtain the biometric information 808. The biometric information 808, for example, may be a fingerprint or footprint obtained by the medical measurement device 20. As the user steps on the weight scale 30, for example, the weight scale 30 may obtain a footprint or pressure print of the user's foot. The medical measurement device 20 may then send the biometric information 808 with the sensor measurement 32. When the health server 22 receives the biometric information 808, the binding application 52 may use the biometric information 808 to determine or infer the user of the medical measurement device 20. The biometric information 808 may also include voice prints using voice recognition technology and/or retinal scans.

The binding application 52 may query the database 34 of health information. As FIG. 24 illustrates, the database 34 of health information may associate the user information 806 to the different users 800. When the health server 22 receives the user information 806, the binding application 52 may query the database 34 of health information for the user information 806. The binding application 52 the retrieves the user 800 that matches the user information 806.

Figure 25:
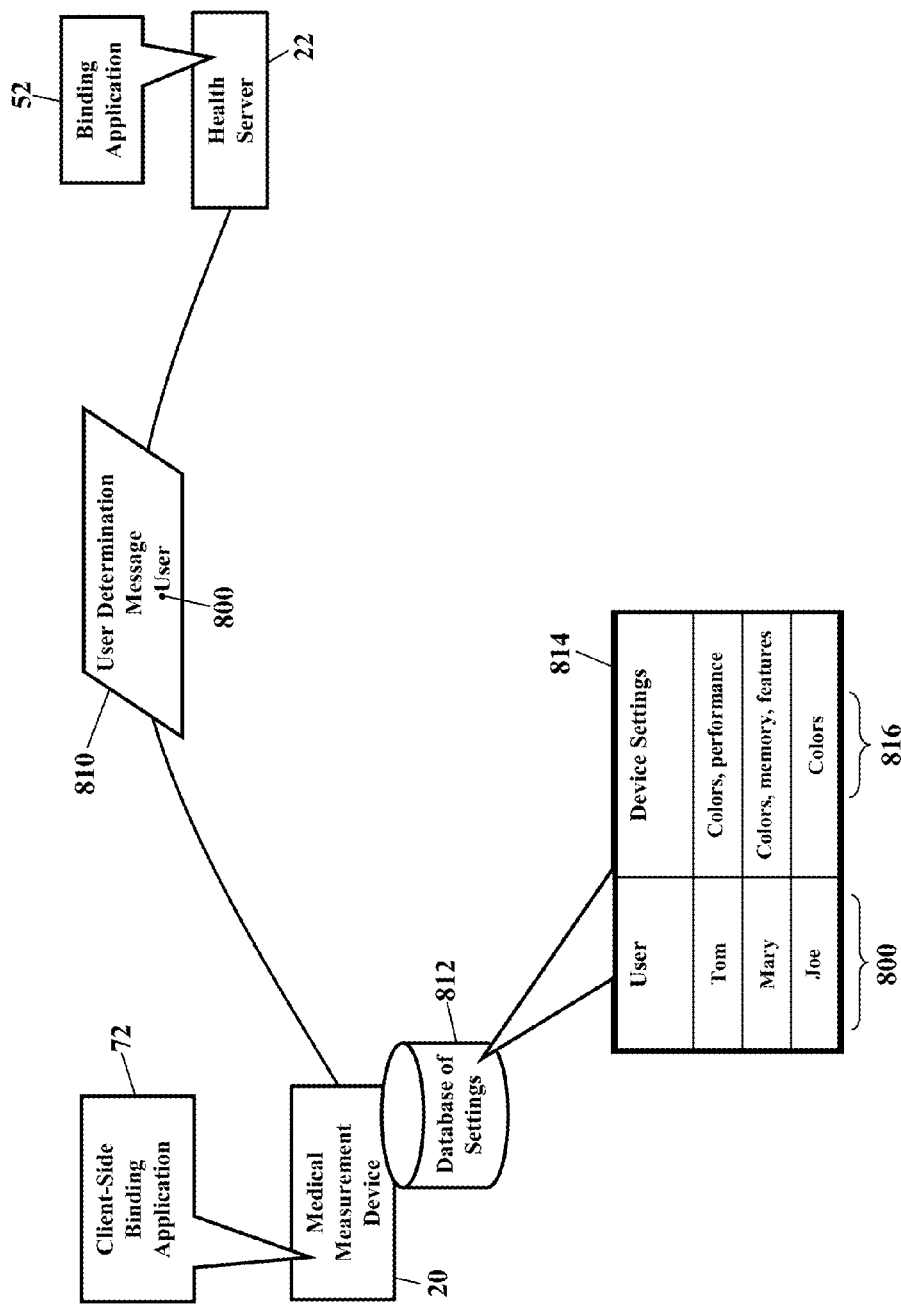

FIG. 25 illustrates personalization of devices, according to more exemplary embodiments. If previous sensor measurements can be confidently matched to a particular user, then the binding application 52 may immediately personalize the medical measurement device 20. Once the user is determined, the binding application 52 may inform the medical measurement device 20 of the determined user. The binding application 52, for example, may send a user determination message 810 to the medical measurement device 20. The user determination message 810 includes or contains information that identifies the user 800 matched to the database 34 of health information. When the medical measurement device 20 receives the user determination message 810, the client-side binding application 72 may then retrieve personalization settings associated with the user 800. The client-side binding application 72, for example, may query a database 812 of settings for the user 800 identified in the user determination message 810. FIG. 25 illustrates the database 812 of settings as a table 814 that maps, relates, or otherwise associates the user 800 to different device settings 816. The device settings 816 represent configuration options that may be personalized for each user 800. The device settings 816 may include, for example, display colors, audible features, and any other options for each user. Once the device settings 816 are retrieved, the medical measurement device 20 may be configured according to the desires of the determined user 800.

Figure 26:
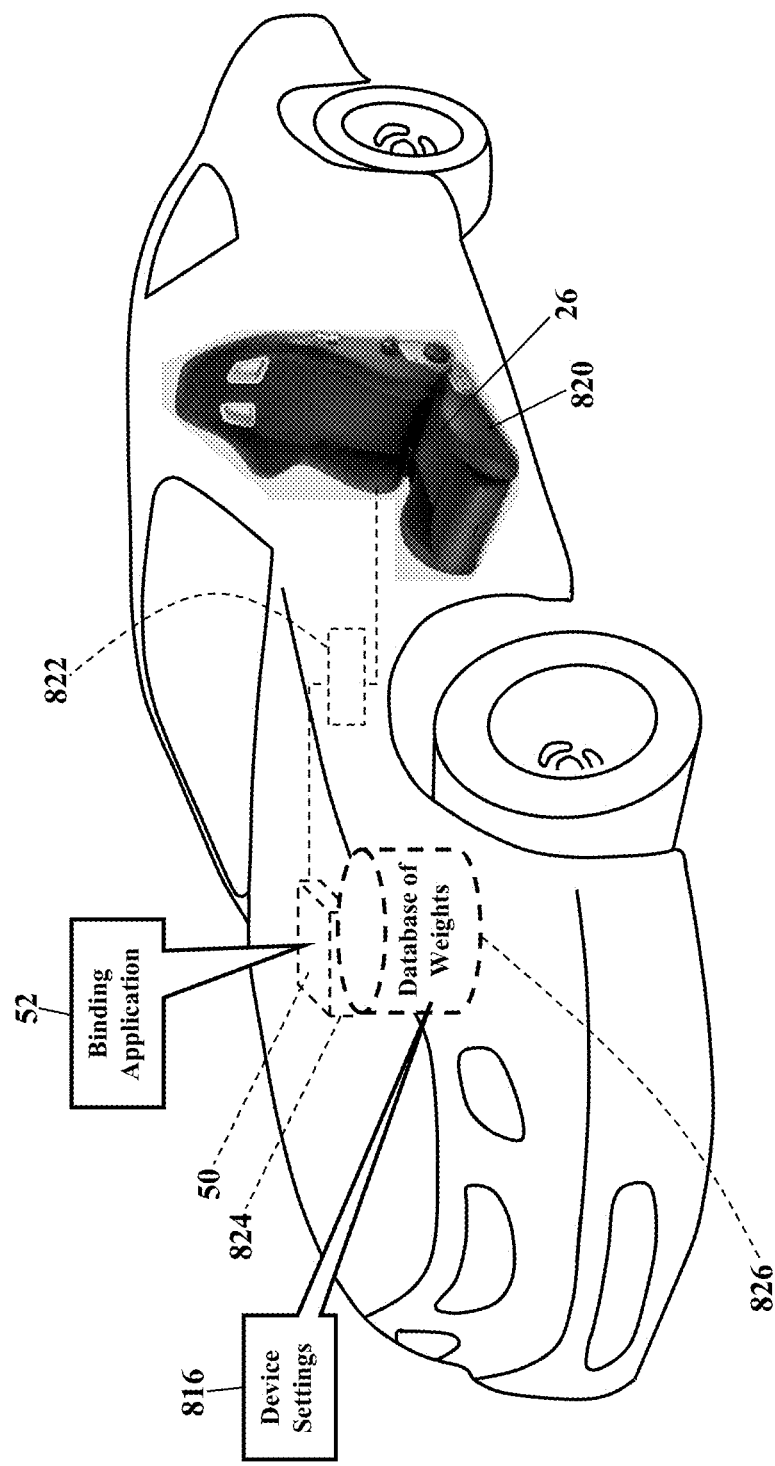

FIG. 26 also illustrates personalization of devices, according to more exemplary embodiments. Here the exemplary embodiments may be used to personalize much more than medical devices. The user determination message 810 may be sent to any device to implement personalization of features. The user determination message 810 may be sent via the communications network (illustrated as reference numeral 24 in FIG. 1) to personalize televisions, seats, cars, audio systems, and any other processor-controlled devices. FIG. 26, for example, illustrates an automotive environment that may be personalized to the determined user 800. Suppose a car seat 820 has the sensor 26 that measures an occupant's weight reading 822. The weight reading 822 (e.g., the sensor measurement 32 illustrated in FIG. 1) is sent to a controller 824 that controls automotive settings. The processor 50 (here operating in the controller 824) executes the binding application 52 and queries a database 826 of weights. The database 826 of weights may be another data table that maps, relates, or otherwise associates different weight readings to the user 800. If the weight reading 822 matches an entry in the database 826 of weights (perhaps using the tolerance 802 and the time limit 804, explained above), then the binding application 52 may retrieve the device settings 816 associated with the user 800. The device settings 816 may represent seating positions, mirror positions, pedal positions, heating and air conditioning settings, audio settings (e.g., favorite channels), and instrument panel options that are preferred by the associated user 800. The device settings 816 may also implement transmission settings, shock absorber settings, speed limits, and other performance settings. The automotive environment, in other words, may be personalized based on the user's weight reading 822.

Personalization also provides assurances. The user of the medical measurement device 20 may be concerned that their physiological data 28 is confidently bound. If the blood pressure, weight, and other physiological data 28 is incorrectly bound to the wrong user, users may quickly lose confidence in the binding application 52. The binding application 52, then, may provide assurances that the user's physiological data 28 is confidently and correctly bound. When the binding application 52 determines the user (as described above), the personalization of the medical measurement device 20 immediately lets the user know of the binding. If the medical measurement device 20, for example, is correctly personalized to the user's liking, then the user should have confidence that their physiological data 28 is correctly bound. If the medical measurement device 20 assumes colors, settings, and messages that are foreign to the user, then the user knows that their physiological data 28 was incorrectly bound. Likewise, if the automotive environment assumes the user's preferred seating position, mirror position, and audio settings, then the user knows their physiological data 28 is correctly bound.

Figure 27:
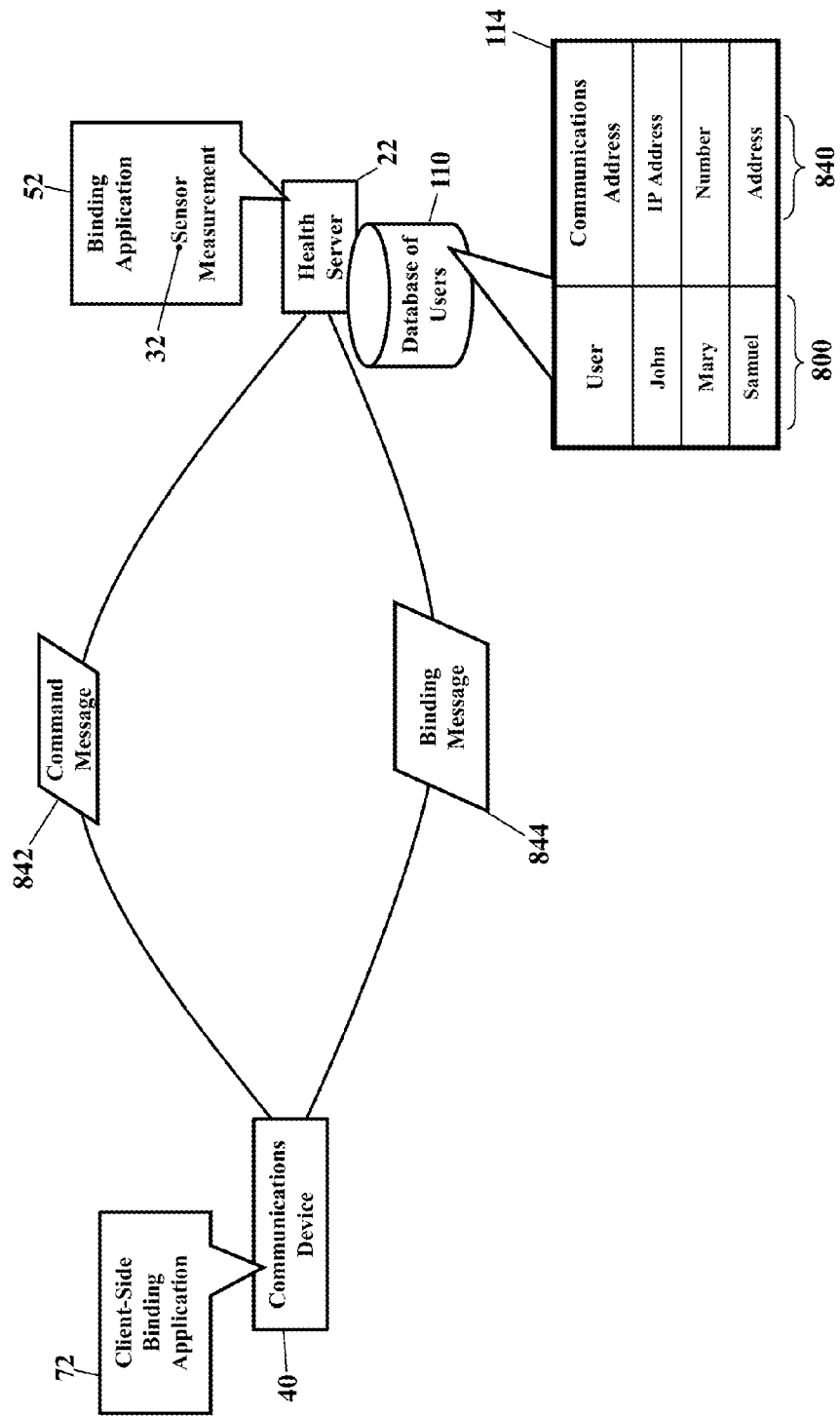
Figure 28:
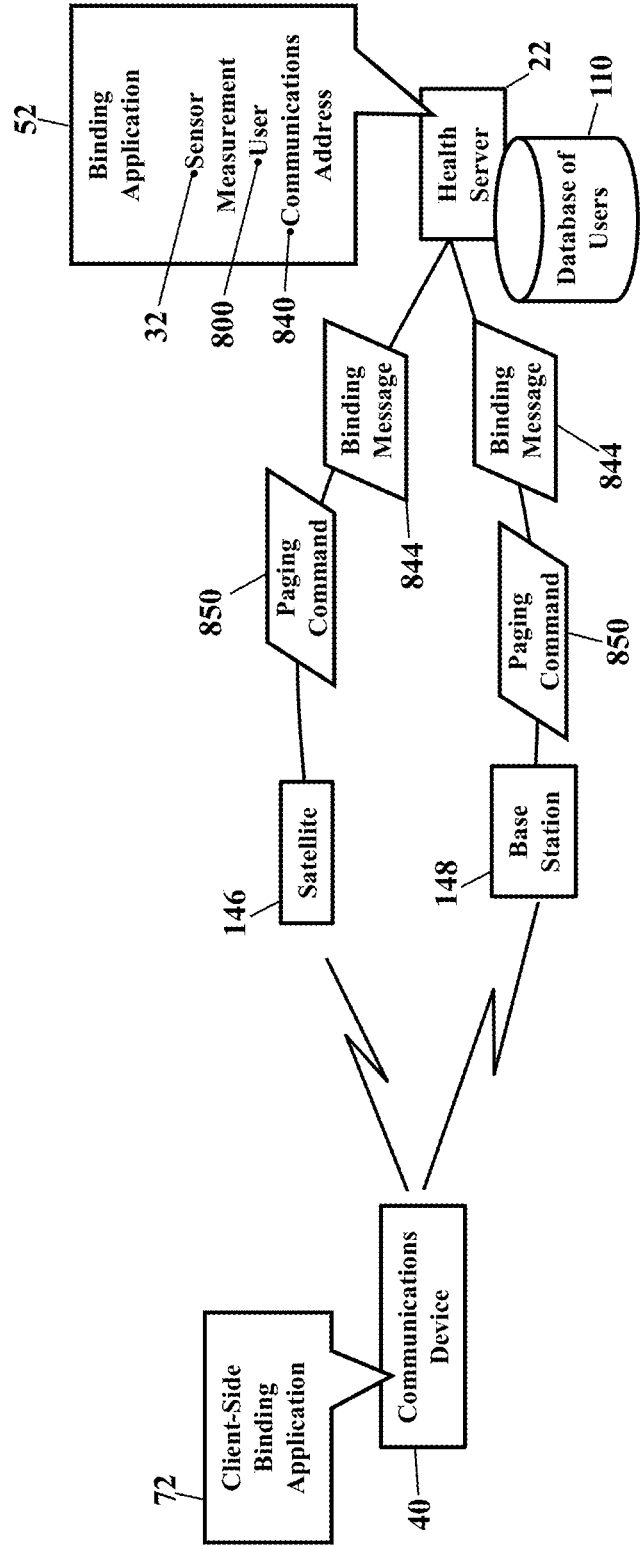
Figure 29:
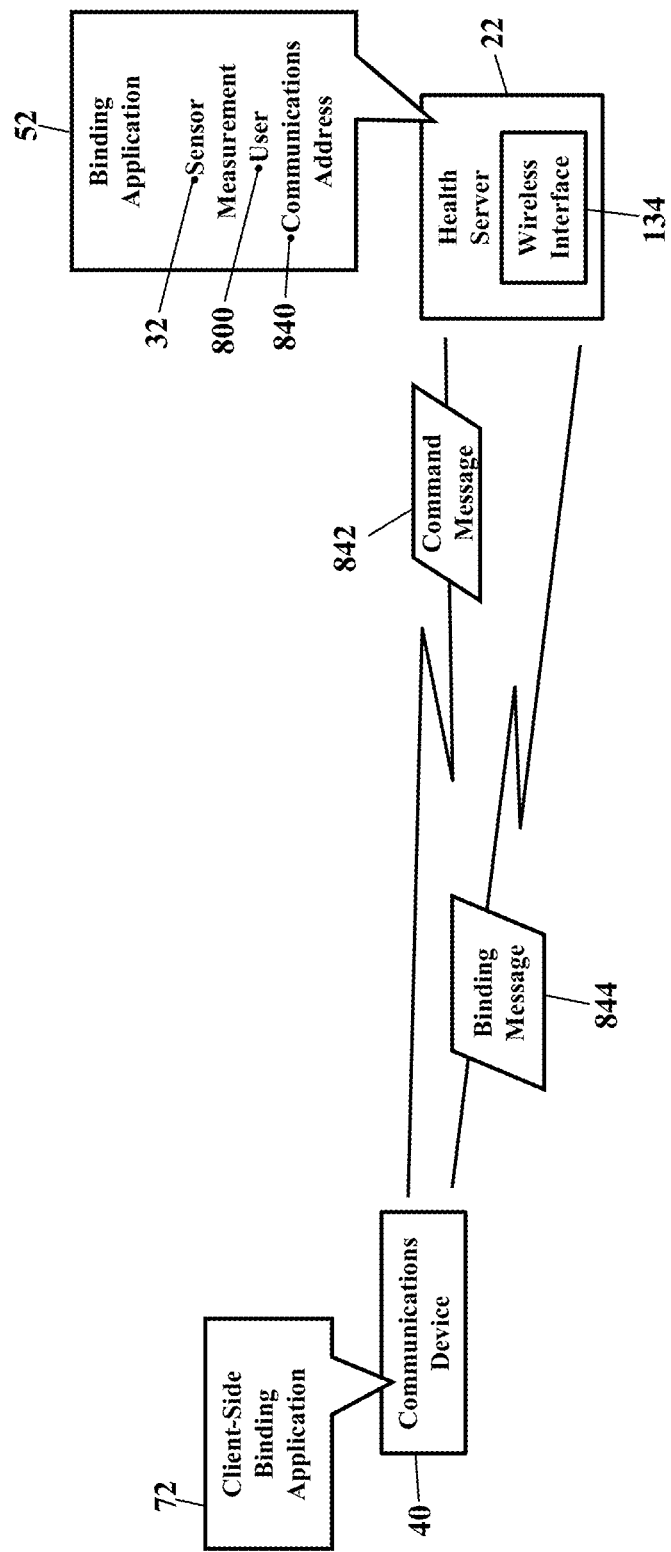

FIGS. 27-29 are schematics further illustrating user binding, according to still more exemplary embodiments. Here the determination of the user 800 may be used to perfect the binding of the sensor measurement 32. Once the sensor measurement 32 is associated to the correct user (as the above paragraphs explained), the user's communications device 40 may be commanded to perfect the binding. As FIG. 27 illustrates, once the user 800 is determined, the database 110 of users may be queried for a communications address 840 associated with the user's communications device 40. The database 110 of users is illustrated as the table 114 that maps, relates, or otherwise associates the different users 800 to communications addresses 840. The binding application 52 queries the database 110 of users for the user 800 (determined from the sensor measurement 32, as above explained). The binding application 52 retrieves the communications address 840 associated with the user 800. The binding application 52 then sends a command message 842 to the communications address 840 associated with the user 800. The command message 842 communicates to the communications address 840 associated with the user's communications device 40. FIG. 27 illustrates the command message 842 communicating to an Internet Protocol address associated with the user's communications device 40 (via the communications network 24 illustrated in FIG. 1). As FIG. 27 also illustrates, though, the command message 842 may communicate to some other number (such as a telephone number) or address associated with the user's communications device 40.

When the client-side binding application 72 receives the command message 842, the command message 842 instructs the client-side binding application 72 to send a binding message 844. The binding message 844 return communicates to the health server 22 and confirms the binding of the sensor measurement 32 to the device identifier 44 associated with the user's communications device 40. The binding application 42, operating in the health server 22, then binds the sensor measurement 32 to the device identifier 44 (as earlier paragraphs explained with reference to FIG. 3). So, FIG. 27 illustrates the binding operation, even if the user does not have their communications device 40. If the user has their weight or blood pressure measured, the binding application 42 may correctly associate the sensor measurement 32 to the user, even if the user does not have their communications device 40.

FIG. 28 illustrates paging commands, according to more exemplary embodiments. Once the sensor measurement 32 is associated to the correct user (as the above paragraphs explained), here the user's communications device 40 may be paged to perfect the binding. Once the user 800 is determined, and the database 110 of users is queried for the communications address 840, the binding application 52 sends a paging command 850 to the communications address 840. The paging command 850 may communicate to the base station 148, and/or to the satellite 146, depending on the network configuration. The paging command 850 instructs the base station 148, and/or the satellite 146, to page the communications address 840 associated with the user's communications device 40. When the client-side binding application 72 receives the page, the client-side binding application 72 returns the binding message 844. The binding message 844 routes to the health server 22 and confirms the binding of the sensor measurement 32 to the device identifier 44 associated with the user's communications device 40 (as earlier paragraphs explained with reference to FIG. 3). Again, then, exemplary embodiments may perfect binding, even if the user does not have their communications device 40.

FIG. 29 illustrates a local area network, according to more exemplary embodiments. Here exemplary embodiments may be implemented in a local area network, such as a home or office environment. The health server 22 again receives the sensor measurement 32, but the binding application 52 must still bind the sensor measurement 32 to a user. Here, then, the binding application 52 may determine what communications devices are within the local area network. Any communications devices proximate to the medical measurement device 20 are more likely to perfect binding.

As FIG. 29 illustrates, when the health server 22 receives the sensor measurement 32, the health server 22 may broadcast the command message 842. The command message 842 communicates to any communications devices in the local area network. FIG. 29 illustrates a near-field wireless broadcast using BLUETOOTH®, WI-FI®, or any other standard. The health server 22 calls or invokes the wireless interface 134 to broadcast the command message 842. The command message 842 communicates to any communications devices within range of the wireless interface 134. The command message 842 may also communicate to any communications devices that physically connect to the local area network. If the command message 842 is received by the communications device 40, the command message 842 instructs the client-side binding application 72 to send the binding message 844. The binding message 844 may wirelessly communicate back to the wireless interface 134, or the binding message 844 may route along cables and/or wires back to the health server 22. Regardless, the binding message 844 is received by the health server 22 and confirms the binding of the sensor measurement 32 to the device identifier 44 associated with the user's communications device 40 (as earlier paragraphs explained with reference to FIG. 3). Again, then, exemplary embodiments may perfect binding, even if the user does not have their communications device 40.

Exemplary embodiments may be physically embodied on or in a computer-readable storage medium. This computer-readable medium may include CD-ROM, DVD, tape, cassette, floppy disk, memory card, and large-capacity disks. This computer-readable medium, or media, could be distributed to end-subscribers, licensees, and assignees. These types of computer-readable media, and other types not mention here but considered within the scope of the exemplary embodiments. A computer program product comprises processor-executable instructions for measuring a user's health, as the above paragraphs explained.

While the exemplary embodiments have been described with respect to various features, aspects, and embodiments, those skilled and unskilled in the art will recognize the exemplary embodiments are not so limited. Other variations, modifications, and alternative embodiments may be made without departing from the spirit and scope of the exemplary embodiments.

The invention claimed is:

1. A method, comprising:
    receiving, by a server, a time-stamped device identifier sent via the Internet from a mobile communications device, the time-stamped device identifier uniquely identifying the mobile communications device;
    receiving, by the server, a time-stamped weight reading sent via the Internet from a weight scale;
    determining, by the server, a difference in time between the time-stamped device identifier and the time-stamped weight reading;
    comparing, by the server, the difference in time to a window of time, the window of time defining a confidence in contemporaneousness between the time-stamped device identifier sent via the Internet and the time-stamped weight reading sent via the Internet; and
    adding, by the server, an electronic entry to an electronic database, the electronic entry electronically associating the time-stamped device identifier to the time-stamped weight reading in response to the difference in time satisfying the window of time.

2. The method of claim 1, further comprising retrieving a group of user identifiers associated with the weight scale.

3. The method of claim 1, further comprising retrieving a group of device identifiers associated with the weight scale.

4. The method of claim 1, further comprising receiving a sensor identifier associated with the weight scale.

5. The method of claim 4, further comprising querying for the sensor identifier.

6. The method of claim 5, further comprising retrieving a group of user identifiers associated with the sensor identifier.

7. The method of claim 1, further comprising retrieving a device multiplier associated with the time-stamped device identifier that expands the window of time.

8. A system, comprising:
    a processor; and
    a memory device, the memory device storing code, the code when executed causing the processor to perform operations, the operations comprising:
    receiving a time-stamped device identifier sent via the Internet from a mobile communications device, the time-stamped device identifier uniquely identifying the mobile communications device;
    receiving a time-stamped weight reading sent via the Internet from a weight scale;
    determining a difference in time between the time-stamped device identifier and the time-stamped weight reading;
    comparing the difference in time to a window of time, the window of time defining a confidence in contemporaneousness between the time-stamped device identifier sent via the Internet and the time-stamped weight reading sent via the Internet; and
    adding an electronic entry to an electronic database, the electronic entry electronically associating the time-stamped device identifier to the time-stamped weight reading in response to the difference in time satisfying the window of time.

9. The system of claim 8, wherein the operations further comprise retrieving a group of user identifiers associated with the weight scale.

10. The system of claim 8, wherein the operations further comprise retrieving a group of device identifiers associated with the weight scale.

11. The system of claim 8, wherein the operations further comprise receiving a sensor identifier associated with the weight scale.

12. The system of claim 11, wherein the operations further comprise querying for the sensor identifier.

13. The system of claim 12, wherein the operations further comprise retrieving a group of user identifiers associated with the sensor identifier.

14. The system of claim 8, wherein the operations further comprise retrieving a device multiplier associated with the time-stamped device identifier that expands the window of time.

15. A memory device storing code that when executed causes a processor to perform operations, the operations comprising:

receiving a time-stamped device identifier sent via the Internet from a mobile communications device, the time-stamped device identifier uniquely identifying the mobile communications device;

receiving a time-stamped weight reading sent via the Internet from a weight scale;

determining a difference in time between the time-stamped device identifier and the time-stamped weight reading;

comparing the difference in time to a window of time, the window of time defining a confidence in contemporaneousness between the time-stamped device identifier sent via the Internet and the time-stamped weight reading sent via the Internet; and adding an electronic entry to an electronic database, the electronic entry electronically associating the time-stamped device identifier to the time-stamped weight reading in response to the difference in time being within the window of time.

16. The memory device of claim 15, wherein the operations further comprise retrieving a group of user identifiers associated with the weight scale.

17. The memory device of claim 15, wherein the operations further comprise retrieving a group of device identifiers associated with the weight scale.

18. The memory device of claim 15, wherein the operations further comprise receiving a sensor identifier associated with the weight scale.

19. The memory device of claim 18, wherein the operations further comprise querying for the sensor identifier.

20. The memory device of claim 19, wherein the operations further comprise retrieving a group of user identifiers associated with the sensor identifier.

* * * * *